(12) United States Patent
Hori et al.

(10) Patent No.: US 11,998,225 B2
(45) Date of Patent: Jun. 4, 2024

(54) METHODS AND APPARATUS FOR CATHETERS, ADAPTABLE TIPS FOR CATHETERS, INCLUDING FOR ASPIRATION CATHETERS, AND ASPIRATION CATHETERS WITH ADJUSTABLE TIPS

(71) Applicant: Q'APEL MEDICAL, INC., Fremont, CA (US)

(72) Inventors: Trevor Hori, Santa Clara, CA (US); Jeffery Krolik, Campbell, CA (US); Edsel San Diego, San Jose, CA (US); John Nguyen, San Jose, CA (US)

(73) Assignee: Q'APEL MEDICAL, INC., Fremont, CA (US)

(*) Notice: Subject to any disclaimer, the term of this patent is extended or adjusted under 35 U.S.C. 154(b) by 0 days.

(21) Appl. No.: 18/379,603

(22) Filed: Oct. 12, 2023

(65) Prior Publication Data
US 2024/0041485 A1 Feb. 8, 2024

Related U.S. Application Data

(63) Continuation of application No. PCT/US2022/044281, filed on Sep. 21, 2022.

(60) Provisional application No. 63/247,102, filed on Sep. 22, 2021.

(51) Int. Cl.
*A61B 17/221* (2006.01)
*A61B 17/22* (2006.01)
*A61M 25/00* (2006.01)

(52) U.S. Cl.
CPC ......... *A61B 17/221* (2013.01); *A61M 25/007* (2013.01); *A61B 2017/22079* (2013.01)

(58) Field of Classification Search
CPC ............ A61M 25/007; A61M 25/0074; A61M 25/0067; A61B 17/221; A61B 2017/22079; A61B 2017/2215; A61B 2017/2217
See application file for complete search history.

(56) References Cited

U.S. PATENT DOCUMENTS

| | | |
|---|---|---|
| 4,202,349 A | 5/1980 | Jones |
| 8,845,677 B2 | 9/2014 | Pal |
| 10,617,435 B2 | 4/2020 | Vale et al. |
| 10,617,436 B2 | 4/2020 | Loganathan |
| 10,729,459 B2 | 8/2020 | Krolik et al. |
| 11,253,291 B2 | 2/2022 | Wallace et al. |

(Continued)

FOREIGN PATENT DOCUMENTS

| | | |
|---|---|---|
| WO | WO 2017/097616 | 6/2017 |
| WO | WO 2021/016213 | 1/2021 |
| WO | WO 2022/020366 | 1/2022 |

OTHER PUBLICATIONS

Schweitzer, John, International Search Report, dated Dec. 13, 2022, 11 pages, Australian Patent Office, Woden ACT Australia.
(Continued)

*Primary Examiner* — James D Ponton
(74) *Attorney, Agent, or Firm* — WILSON SONSINI GOODRICH & ROSATI

(57) ABSTRACT

Methods and apparatus for evaluating and manipulating objects in a body, for example emboli in a body lumen are described, and in some examples methods and apparatus use adaptable tips on catheters, for example aspiration catheters, for manipulating and/or removing such emboli.

20 Claims, 13 Drawing Sheets

(56) References Cited

U.S. PATENT DOCUMENTS

| | | |
|---|---|---|
| 11,406,403 B2 | 8/2022 | Casey et al. |
| 2006/0264972 A1 | 11/2006 | Mulholland et al. |
| 2019/0038365 A1 | 2/2019 | Soper et al. |
| 2020/0164117 A1 | 5/2020 | Culhane et al. |
| 2020/0281611 A1 | 9/2020 | Kelly et al. |
| 2020/0390460 A9 | 12/2020 | Casey et al. |
| 2021/0077116 A1* | 3/2021 | Ferrera ................ A61B 17/221 |
| 2021/0153884 A1 | 5/2021 | Casey et al. |
| 2021/0275197 A1 | 9/2021 | Vale et al. |
| 2021/0307766 A1 | 10/2021 | Keating et al. |
| 2022/0125450 A1 | 4/2022 | Sirhan et al. |
| 2022/0192688 A1 | 6/2022 | Olsen et al. |
| 2022/0257260 A1 | 8/2022 | Hewitt et al. |
| 2022/0265294 A1 | 8/2022 | Ulm, III |

OTHER PUBLICATIONS

Schweitzer, John, Written Opinion of the International Searching Authority, dated Dec. 13, 2022, 11 pages, Australian Patent Office, Woden ACT Australia.

* cited by examiner

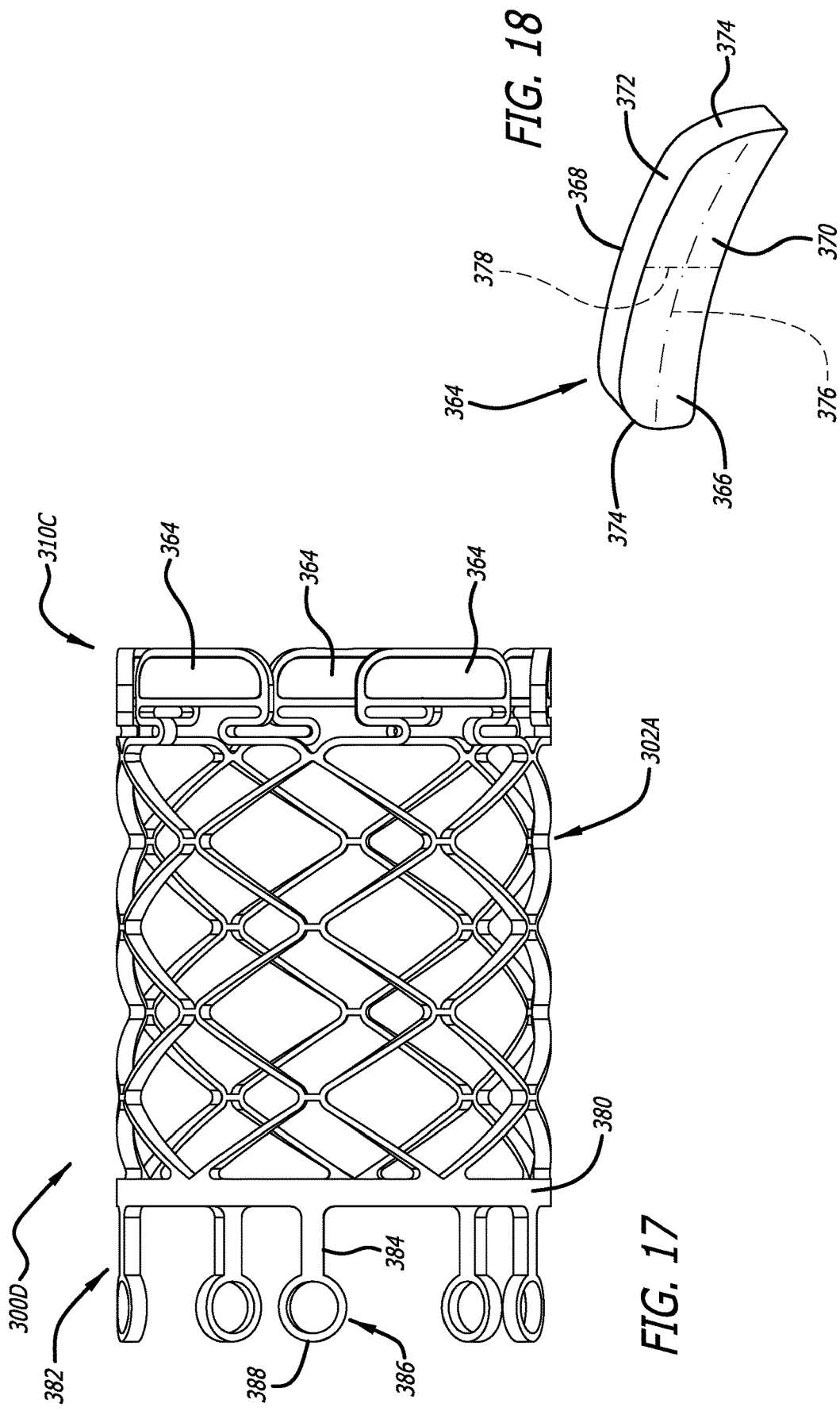

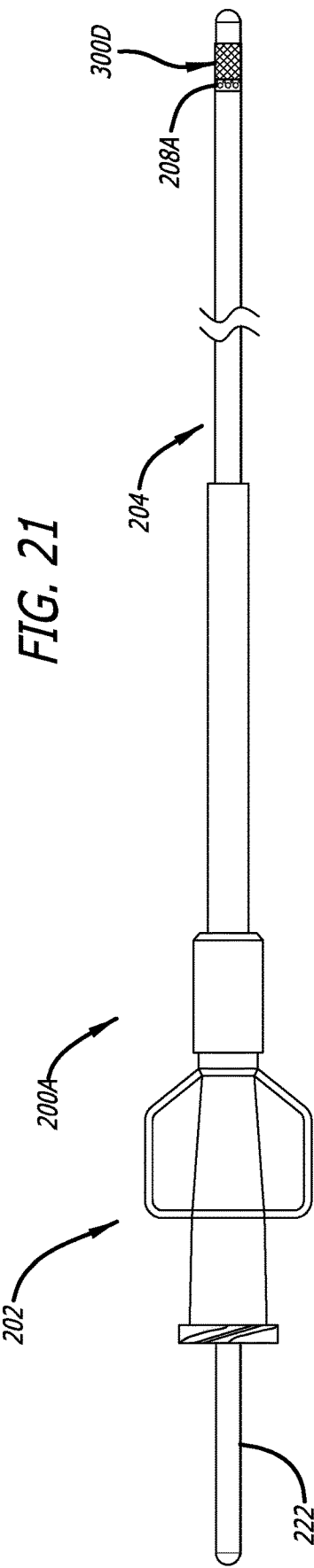
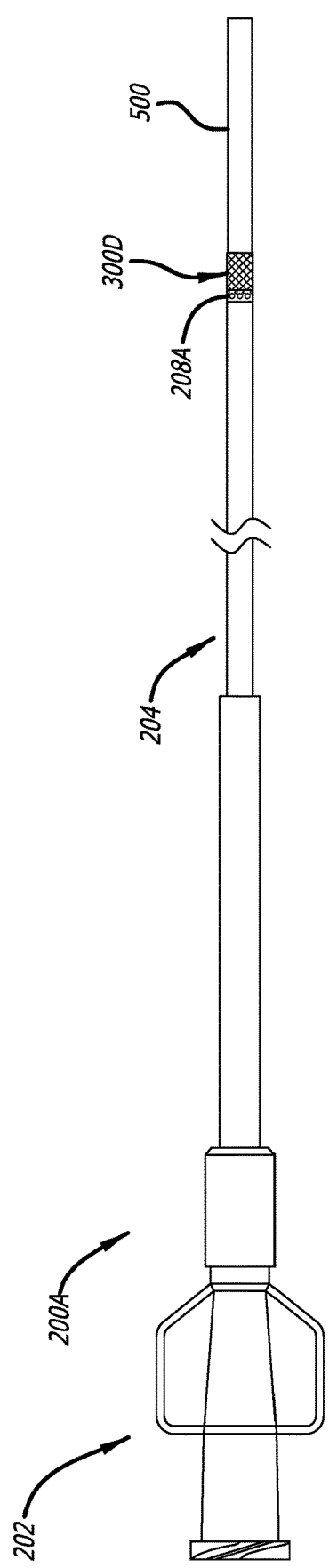
FIG. 21
FIG. 22

METHODS AND APPARATUS FOR CATHETERS, ADAPTABLE TIPS FOR CATHETERS, INCLUDING FOR ASPIRATION CATHETERS, AND ASPIRATION CATHETERS WITH ADJUSTABLE TIPS

CROSS REFERENCE TO RELATED APPLICATIONS

This is a continuation of Serial No. PCT/US2022/044281 filed Sep. 21, 2022, published as WO2023/049203 on Mar. 30, 2023, which claims priority to Ser. No. 63/247,102 filed Sep. 22, 2021, the content and publications of which are incorporated herein by reference.

FIELD

These inventions relate to methods and apparatus for manipulating objects, for example emboli or stones, in a body lumen, and in some examples methods and apparatus using adaptable tips on catheters for manipulating such objects, which may include methods and apparatus for visualizing or evaluating interactions between catheters and objects such as emboli or stones.

BACKGROUND

Aspiration is commonly used in procedures where a blockage in a body lumen prevents normal body function. One example of an object causing the blockage is sometimes referred to as an embolus. In this aspiration procedure, an elongated tube or catheter is commonly inserted to the location where the blockage has occurred, and a suction force or reduced fluid pressure is applied to the inner lumen of the catheter to attempt to remove the emboli.

A successful outcome of this procedure may be the aspiration of the emboli through the lumen of the catheter, thus resolving the blockage. Another successful outcome may be the adherence of the embolus to the tip of the catheter due to the suction force applied, wherein the catheter and embolus can be removed from the body lumen together, thus resolving the blockage.

In the case where the procedure is unsuccessful, the embolus 80 (FIG. 2) will not engage with the tip 82 of the catheter 84 sufficiently to be either aspirated through the catheter lumen 86, nor have sufficient adherence to the tip of the catheter so that it can overcome the forces keeping the embolus in place within the body lumen 88. The failed aspiration may be caused by an angular mismatch between the distal tip 82 of the catheter and the face of the embolus as shown in FIG. 2. In this case, the suction force of aspiration is not transferred to the face of the embolus because the orifice at the tip of the catheter does not form a suitable seal with the emboli 80. Another case of failed aspiration can be seen in FIG. 3, where the embolus 90 has an irregular surface that prevents the suction force of aspiration to be transferred to the face of the embolus.

SUMMARY

Apparatus and methods are described for assisting in manipulating objects in the body, including for example a body lumen, and including for example unwanted objects such as emboli or stones. In one example, an adaptable tip for a catheter includes a portion for engaging the object in the body, and in one example the adaptable tip is on a distal end portion of an aspiration catheter. In the foregoing examples, the adaptable tip may include a frame, skeleton, or network structure (referred to herein collectively as "frame") that is axially flexible, and in some examples axially resiliently flexible, for example having a restoring function similar to a spring function. In any of the foregoing examples, the frame may be both axially and radially flexible, including resiliently flexible. Also in any of the foregoing examples, the frame can have a number of configurations, including one or more helical configurations, a frame having multiple nodes, a frame having struts forming parallelograms and/or a frame having multiple linear struts, adjacent ones of which are coupled at respective nodes. In any of the foregoing examples, the frame can be formed so that axial reduction of a length of the frame results in a reduction in an inside diameter of the frame, and in another frame configuration axial reduction of a length of the frame results in an increase in an inside diameter of the frame. In any one or more of the foregoing examples, the frame is axially bendable or movable so that a central axis of the frame can be bent or curved. Therefore, in one or more of the examples of a frame, the frame can be axially, directionally and/or radially variable during normal use, for example changing from a neutral configuration to a flexed and/or compressed configuration. In any of the foregoing examples, the frame may be embedded or encased in or surrounded by an elastic polymer material, for example a fluid impermeable material to form a shroud or cover for the external surface of the frame. The elastomeric polymer material helps to ensure transmission of a reduced pressure or suction to the distal tip of the assembly.

In any of the foregoing examples, a movable tip for a distal end portion of a catheter may include a base portion for engaging the distal end portion of the catheter. In one configuration, the base portion extends over or about portions of the distal end portion of the catheter, and typically around the entire perimeter of a distal portion of the catheter. In one example, the base portion is a circular ring, extending around an axis of the movable tip, for example completely 360° around the distal end portion of the catheter. In a further configuration, the base portion is a solid circular or annular element and has a cross-sectional area that is greater than a cross-sectional area of the other elements of the movable tip, for example greater than the cross-sectional area of struts forming a frame of the tip. In an additional or alternative configuration, the base portion can include one or more proximally extending support elements for engaging suitable portions of the distal end portion of the catheter. For example, a proximally extending support element may include a key element for engaging a complementary structure or geometry in the distal end portion of the catheter. In one example, the key element may be a nonlinear portion, for example a partly or completely circular portion or other geometry that is nonlinear and that would assist in reliably securing the movable tip and the catheter distal end portion together. In a further example, the key element may include an opening, for example to allow entry of a film or other material into the opening to help secure the movable tip in place.

In any of the examples herein, the frame of the adaptable tip may take a number of configurations. In one configuration, the frame is formed from a plurality of helically extending frame elements extending between the base ring and the plurality of engagement or contacting structures or extensions. Helical frame elements allow resilient compression of the adaptable tip, for example when an object presses against the adaptable tip. In one example, each of the helically extending frame elements is substantially continuous, between the base ring and the engagement or contacting structures or extensions, and each frame element has substantially the same pitch. In one example, there is an odd number of helical frame elements forming the frame. In another configuration, the frame includes a plurality of helically extending frame elements where adjacent frame elements are linked to each other. In one example of linked frame elements, a first plurality of helically extending frame elements are coupled to a second plurality of frame elements extending helically in an opposite direction. In one example, the linked frame elements form parallelogram geometries, with a plurality of parallelogram geometries combining to form the frame structure. In one configuration, 2½ parallelogram structures in the axial direction form the length of the frame, and five parallelogram structures take up the circumference, providing a total of 25 parallelograms. In one configuration, the plurality of parallelograms are formed from struts wherein adjacent struts are connected to each other at respective nodes. A node may include a bridge or connecting structure, for example between pairs of struts. Struts of the frame may be connected to the base ring at nodes, and/or engagement or contacting structures or extensions may be connected to the frame at nodes. Combinations of struts and nodes may form a closed cell frame.

In any of the examples of the frame provided herein, the frame is formed in an unbiased or neutral configuration when in a free state, or when the frame is unconstrained circumferentially. For example, the frame can be formed as a monolithic structure from a monolithic tube with the base ring and a plurality of struts and nodes, in a conventional manner such as by laser cutting. With the frame as a full rotation about the central axis, having the shape of a cylinder, the frame can keep its shape, especially when secured on a distal end of a catheter, until it is placed in compression or possibly tension with an axial or sideload or combination thereof.

In any of the foregoing examples, the adaptable tip may include one or more engagement or contacting structures, or extensions, for example on a distal portion of the adaptable tip, for engaging or contacting the object in the body. For example, a distal portion of the adaptable tip may include one or more axially and/or radially flexible, for example resiliently flexible, elements. The element or elements can be configured to contact or engage respective surface portions of the object, for example to assist in manipulating the object within the body and/or evaluating the configuration of the object, for example when contact is made with the object and/or as the object is moved within the body. In these examples, the engagement or contacting structures or structure is configured to extend or move either or both axially and radially an amount relative to a central axis of the frame. While the engagement or contacting structures can be different from at least one of the other engagement or contacting structures on the tip, the present examples of engagement or contacting structures are substantially identical and are resiliently flexible both axially and radially relative to a central axis of the frame. In one configuration, the engagement or contacting structures pivot about respective axis regions that are on approximately chords of a hypothetical cylinder or circle, for example so that the structures can move outward, for example independently of each other, and to accommodate surface configurations of objects with which they come into contact. In the present examples, the engagement or contacting structures are also covered or coated by the elastic polymer material covering the frame, for example to ensure the transmission of a suction past the engagement or contacting structures.

In any of the foregoing examples, the engagement or contacting structures or extensions may include a torsion section, which may include at least one strut extending in a plane perpendicular to the axis of the tip. The at least one strut can extend circumferentially or arcuately, and may help to define an axis area about which the extension may pivot, for example radially outward. In another example, an extension may include a torsion section with first and second struts extending circumferentially or arcuately, and when the first and second struts are in the same plane, they may help to define a pivot axis area for the extension to move radially outward and back. In a further example, an extension may include a plurality of struts extending circumferentially or arcuately, some of which are coplanar with each other, and the plurality of struts may form part of a torsion section and help to allow the extension to pivot as desired. In one configuration, at least some and in one example all of the struts have the same cross-sectional area, and may also have the same cross-sectional area as other structures in the adaptable tip, such as struts in a medial frame.

Additionally, in any of the foregoing examples, any or all of the engagement or contacting structures or extensions may be separated from each other by a gap between adjacent structures or extensions. Where the adaptable tip is coated with a polymer, the size of the gap between adjacent structures or extensions will affect the flexibility of the structures or extensions. In one example, the engagement or contacting structure or extension extends circumferentially a first distance and adjacent structures or extensions are separated by a gap of a second distance and a ratio of the first distance to the second distance may range from less than one to greater than one. In one configuration, the ratio is greater than or equal to one, and for example greater than or equal to one and less than or equal to six. In some configurations, the ratio is selected to be two. In a further example, movement of the engagement or contacting structures or extensions is selected to be easier in a radially outward direction than in a circumferential or arcuate direction. For example, the engagement or contacting structures or extensions may be more flexible radially outward than they are in a circumferential direction.

In any of the foregoing examples, the frame and/or any or all of the engagement or contacting structures or extensions may include one or more radiopaque indicators or markers (collectively referred to herein as "markers"). In any one or more of the foregoing examples, one or more markers are included on respective engagement or contacting structures or extensions at a distal portion of a frame. In one example, a marker is supported by each engagement or contacting structure or extension on a frame, and configured in such a way that the marker can move with the engagement or contacting structure or extension. Each marker may be substantially identical to one or more or all of the other markers, or a marker can be different from at least one other marker for visualization or differentiation during use. The marker or markers may be round or circular discs, but in at least some of the examples, the marker or markers are non-circular or are asymmetric about an axis through a center of a marker. In one example, the marker or markers are approximately rectilinear, for example non-square with rounded corners. Also, one or more markers may be non-planar, for example concave in at least a first dimension, for example concave relative to a central axis of a catheter tip on which the marker or markers are positioned. In one example, a marker is non-planar in a first dimension, for example concave relative to a central axis of a catheter tip, and has an otherwise generally partially cylindrical profile, for example conforming to the cylindrical shape of the adaptable tip.

In any of the foregoing examples, a marker can be supported by a marker holding frame, and the marker holding frame can be coupled to one or more struts in the engagement or contacting structures or extensions. In one example, a marker holding frame can be supported by respective arcuate strut elements for example having the same cross-sectional area as other struts in the adaptable tip, but having a curvature rather than being straight. In another example, a marker holding frame can have elements with respective cross-sections greater than that of struts supporting the marker holding frame.

In any of the foregoing examples, a marker can be a conventional marker, such as a flat and circular marker, while in other examples one or more of the markers or all of the markers can be other geometries, including non-circular and/or nonplanar. One example of a noncircular marker is an oval or rectilinear marker, for example having a geometry with perpendicular axes where one axis is a different length than the other axis, such as a major and a minor axis. For example, the marker can extend a first distance in a plane perpendicular to the tip axis greater than a second distance in a direction parallel to the tip axis, for example so that the marker can have a greater visibility in the circumferential direction than the axial direction. In one example, the first distance is approximately four times the second distance. In a further example, one or more or all of the markers are non-planar. For example, the marker or markers can conform to the geometry of the cylindrical shape of the adaptable tip. In a further example, the marker or markers can be asymmetric about a plane perpendicular to the tip axis, for example where a distal portion of the marker has a geometry different than a proximal portion of the marker, for example rounded corners versus substantially square corners.

Furthermore in any of the foregoing examples, the adaptable tip can be coated with a polymeric material, for example an elastomeric fluid impermeable coating. The coating can be configured to prevent fluid from passing through the frame and between the frame and the engagement or contacting structures or extensions. The coating may substantially embed the base ring and frame and engagement or contacting structures or extensions in the polymeric material. For example, the thickness of the polymeric material may be less than the wall thickness of the base ring, frame and structures or extensions, for example approximately one third the wall thickness of the base ring, frame and structures or extensions. A proximal portion of the coating may extend from an axial position proximal of the base ring to an axial position distal of the engagement or contacting structures or extensions.

In any one or more of the foregoing examples, the one or more structures are used with a catheter, for example an aspiration catheter. A catheter assembly formed of a catheter having a lumen extending to a distal end portion and an adaptable tip as described herein supported on the distal end portion of the catheter can be used on objects in the vasculature, for example emboli. The adaptable tip can be supported on the catheter by inter-engagement, attachment or other securement. In one example, the adaptable tip can be supported on the catheter through a support ring, which also may be a radiopaque marker. The support ring may include structures complementary to structures on the base ring of the tip to promote secure positioning of the tip on the distal end portion of the catheter. For example, the structures on the support ring may be keyed to structures on the base ring. In one configuration, the support ring may include circular openings for receiving circular extensions on the base ring of the tip. Additionally or alternatively, welding, adhesive or plastic coating may be used to secure the tip and the catheter together.

During use, a catheter having an adaptable tip according to any of the foregoing examples is coupled to an aspiration system, and the tip positioned adjacent an object in the body. With an aspiration catheter having markers on a distal portion of an adaptable tip, the user may be able to view and evaluate a configuration of a portion of the object based on visualization of the markers. A user may also be able to evaluate the relative position and orientation of the assembly. With markers on axially and/or radially flexible elements on the adaptable tip, a user may be able to view and evaluate a configuration of a portion of the object in multiple dimensions, for example when the object is in a position in the body and/or as the object is being moved in the body.

These and other examples are set forth more fully below in conjunction with drawings, a brief description of which follows.

BRIEF DESCRIPTION OF THE DRAWINGS

FIG. 17 is a side elevation view of the adaptable tip of FIG. 14 with markers.

FIG. 18 is an upper isometric view of a marker for use with the adaptable tip of FIG. 17.

FIG. 21 is a side elevation view of an aspiration catheter such as that shown in FIG. 1 with a mandrel for assembly of the catheter.

FIG. 22 is a side elevation view of a completed aspiration catheter and a removable protective cover for the distal end portion of the catheter.

DETAILED DESCRIPTION

Figure 1:
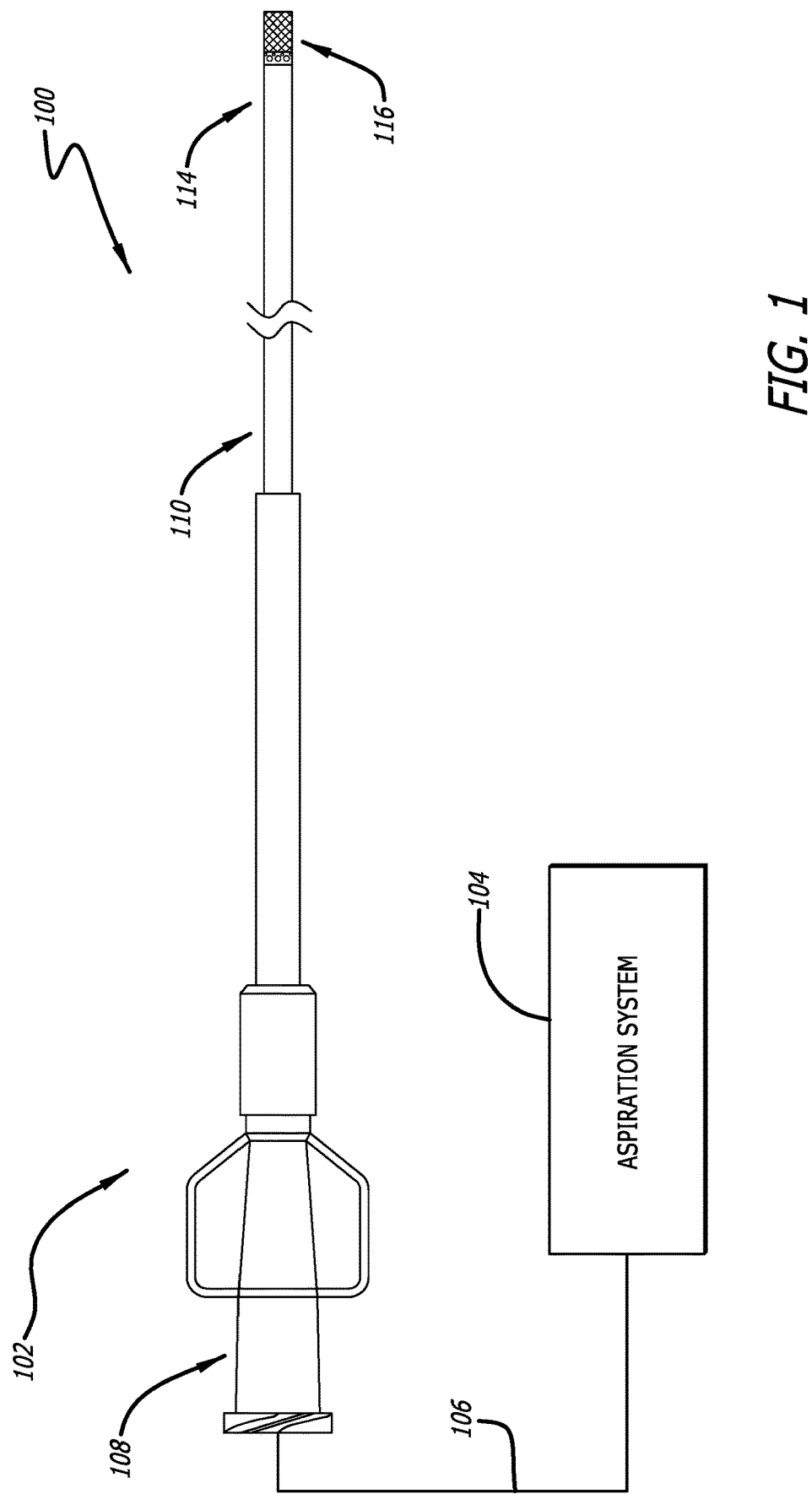
FIG. 1 is a side elevation view and schematic of an aspiration assembly with an aspiration catheter and adaptable tip according to one example described herein.
Figure 2:
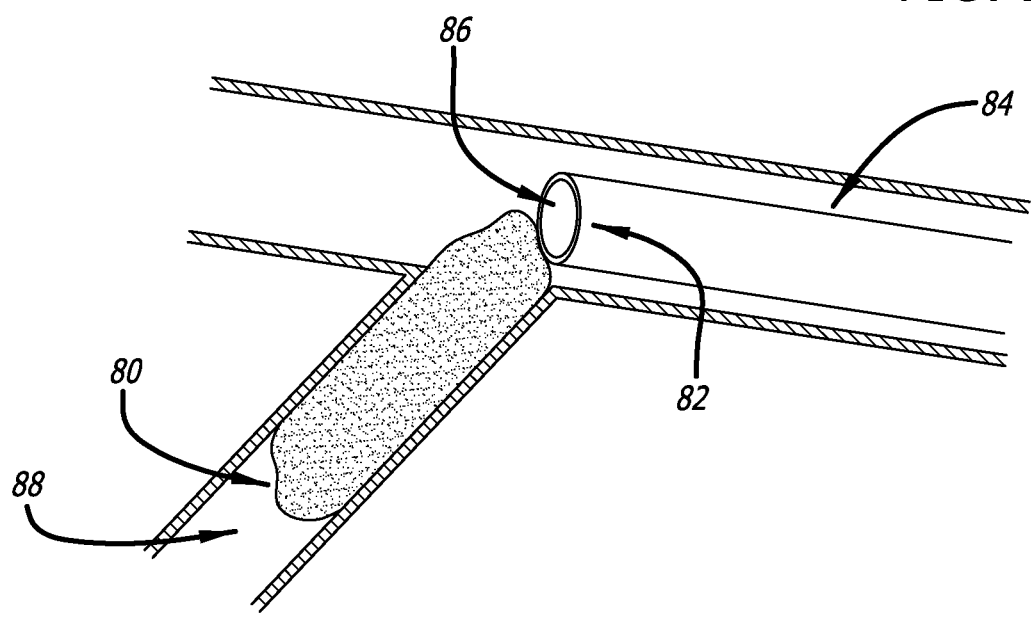
FIG. 2 is a schematic of an example of a catheter adjacent to an object in the body, for example a body lumen.
Figure 3:
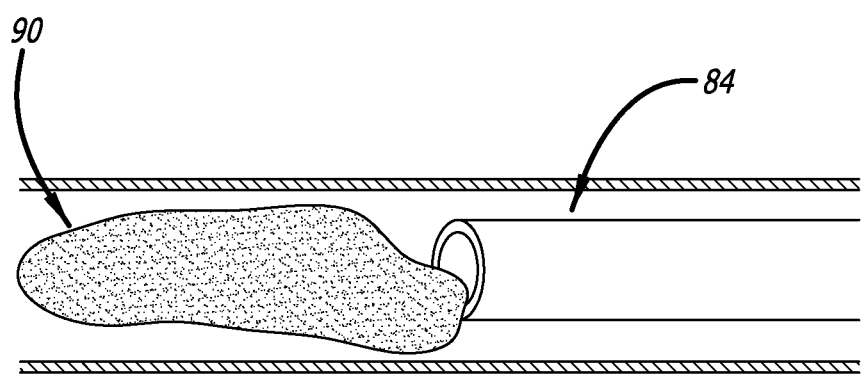
FIG. 3 is a schematic of another example of a catheter adjacent to an object in the body, for example a body lumen.

This specification taken in conjunction with the drawings sets forth examples of apparatus and methods incorporating one or more aspects of the present inventions in such a manner that any person skilled in the art can make and use the inventions. The examples provide the best modes contemplated for carrying out the inventions, although it should be understood that various modifications can be accomplished within the parameters of the present inventions.

Examples of adaptable tips and of methods of making and using the adaptable tips are described, in several examples with aspiration catheters and an aspiration system. Depending on what feature or features are incorporated in a given structure or a given method, benefits can be achieved in the structure or the method. For example, adaptable tips using a helical frame provide an axially variable and radially variable structure for contacting an object in the body. Similarly, adaptable tips using struts interconnected by nodes, in one example to provide a network of parallelograms in three dimensions, provide an axially variable and radially variable structure for contacting an object in the body. Also, adaptable tips having axially and/or radially movable engagement or contacting elements or extensions can more reliably contact or engage an object in the body. Additionally, adaptable tips having one or more markers, including for example markers on medial portions and/or on movable engagement or contacting elements or extensions, provide ways to observe and evaluate movement of the adaptable tip and to observe and evaluate characteristics of an object in the body, both in place and while the object moves.

These and other benefits will become more apparent with consideration of the description of the examples herein. However, it should be understood that not all of the benefits or features discussed with respect to a particular example must be incorporated into an adaptable tip, component or method in order to achieve one or more benefits contemplated by these examples. Additionally, it should be understood that features of the examples can be incorporated into an adaptable tip, component or method to achieve some measure of a given benefit even though the benefit may not be optimal compared to other possible configurations. For example, one or more benefits may not be optimized for a given configuration in order to achieve cost reductions, efficiencies or for other reasons known to the person settling on a particular product configuration or method.

Examples of a number of adaptable tip configurations and of methods of making and using the adaptable tips are described herein, for example for use in aspiration catheters or other object retrieval catheters, and some have particular benefits in being used together. However, even though these apparatus and methods are considered together at this point, there is no requirement that they be combined, used together, or that one component or method be used with any other component or method, or combination. Additionally, it will be understood that a given component or method could be combined with other structures or methods not expressly discussed herein while still achieving desirable results.

As used herein, "substantially" and "approximately" shall mean the designated parameter or configuration, plus or minus 10%. However, it should be understood that terminology used for orientation or relative position, such as front, rear, side, left and right, upper and lower, and the like, may be used in the Detailed Description for ease of understanding and reference, and might not be used as exclusive terms for the structures being described and illustrated.

The present inventions overcome limitations of existing catheters, including for example aspiration catheters, by providing an improved tip that is highly adaptable to unwanted objects, such as emboli during aspiration or stones. In one example of an aspiration assembly 100 (FIG. 1), the assembly may include an aspiration catheter assembly 102 operated in conjunction with an aspiration system 104. The aspiration system is a conventional aspiration device currently commonly available with a suitable controller and user interface (not shown) for allowing the user to operate the system for controlling vacuum or decreased pressure in a fluid line 106 communicating with a lumen in the catheter assembly 102 through a hub 108. The hub supports a catheter body 110 having an internal lumen 112 extending from the hub 108 to a distal end portion 114. In the examples described herein, the distal end portion 114 supports an adaptable tip 116, examples of which are described more fully below. The adaptable tip 116 can take a number of configurations, including the examples described herein. Other catheters with or without aspiration may be used with the adaptable tips described herein, for example catheters for retrieving or accessing other unwanted objects such as stones (litholapaxy).

In one example of a catheter assembly, for example an aspiration catheter assembly, an aspiration catheter 200 (FIG. 4) includes a proximal hub 202 that provides access to the central lumen 112 of the catheter. The catheter also includes a body or shaft 204 that comprises the majority of the length of the catheter. The hub and the catheter body are conventional constructions for aspiration catheters, wherein the hub is configured for coupling to an aspiration system 104 and manipulation and control by the user, and the body is configured for easily transiting vasculature including intracranial vasculature and for receiving and following guide devices commonly used in conjunction with aspiration catheters. The internal diameter of the lumen, for example, may be the conventional 0.071 or 0.072 inches, but it is understood that the features of an adaptable tip can be successfully used on a number of catheter configurations.

Figure 5:
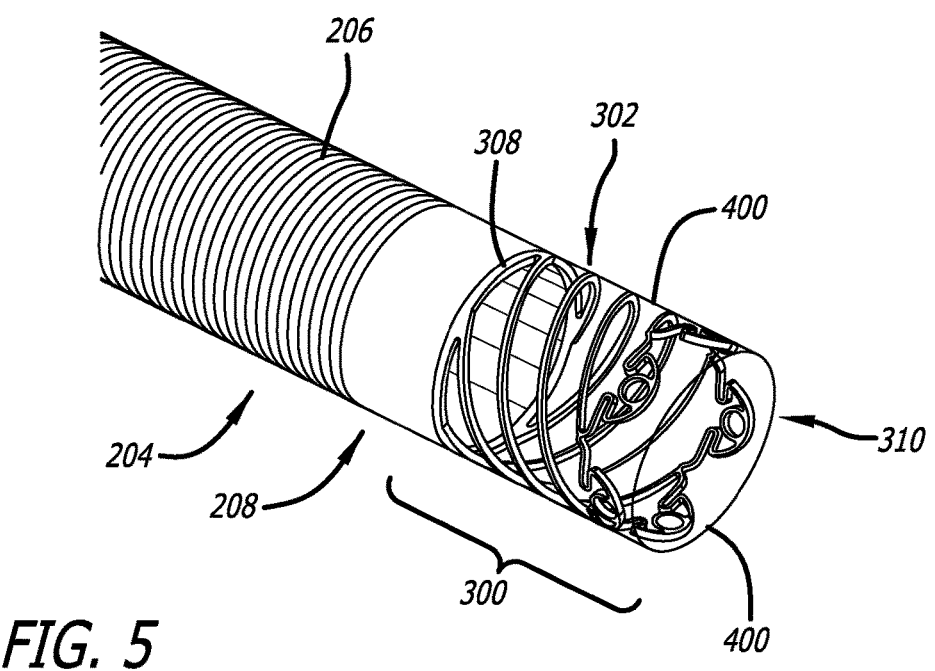
FIG. 5 is an upper right perspective view of a distal portion of the aspiration catheter of FIG. 4 with an example of an adaptable tip on a distal end portion of the catheter.

In one illustrated configuration (FIG. 5), the catheter shaft 204 includes a reinforcement coil or braid 206 or similar construction to provide support against ovalization or kinking of the shaft during navigation of the tortuous vasculature. The illustrated catheter also includes a conventional marker band 208, positioned distal to the shaft 204. The marker band provides easy visualization of the tip of the catheter when viewed under fluoroscopic guidance. Alternatively, any of the catheter configurations can include an alternative marker band such as that described herein or alternatives thereof.

A number of tip configurations can be used on catheters, for example on aspiration catheters as described herein. A tip can improve the ability of a catheter to interact with objects in vasculature or other body regions, including for example with emboli, and can also improve visualization of a catheter procedure and environment, including those for example for use in removing emboli or other objects or otherwise acting on such objects.

In one example of a tip for a catheter, for example an aspiration catheter, a tip 300 (FIGS. 4-10) is supported on a distal end portion of the catheter 200, for example distal of the marker band 208. The tip is an adaptable tip that serves to engage objects, for example an embolus, so that it may be evaluated and/or aspirated through the catheter lumen or engaged and removed with the catheter.

In the illustrated configuration, the tip includes a medial frame 302 extending distally of the distal tip portion of the catheter and circumferentially about a central axis 304 (FIG. 10) of the tip. In the examples described herein, the central axis 304 of the tip is the same as the central axis of the distal end portion of the catheter/marker ring 208. Additionally, in the examples described herein, the inside diameter of the tip frame 302 is approximately the same as the inside diameter of the body lumen. In the examples described herein, the inside diameter of the tip is 0.073 inch, and the outside diameter is 0.079 inch, for example the same outside diameter of the distal end portion of the catheter on which is supported. In some examples of the tip, the tip is configured to have a smaller outside diameter than the vessel lumen through which it will traverse, and in the neutral state, the outside diameter will be substantially constant until it engages an object, for example. When the tip is deployed over a navigation catheter for example, having a stable configuration and staying in the neutral state during deployment until it extends beyond the navigation catheter and engages an object is desirable.

In the example illustrated in FIGS. 4-10, the frame 302 includes a plurality of helically extending frame elements 306. In the present example, each frame element extends substantially continuously in the same direction at approximately the same pitch as the other frame elements, and the pitch is substantially constant over the axial length of the frame, but the frame element pitches can be different from each other and they can vary over the axial length of the frame, for example depending on desired configuration for the frame.

The frame 302 and frame elements 306 are resiliently flexible, and they are compressible when an axial or off-axis load or force is applied from the distal direction. The frame is formed from a material, such as nitinol, that is resiliently flexible, allowing compression of the frame and returned to its original configuration after a compressive load is removed. Compression of one or more of the frame elements 306 tends to reduce the inside diameter of the frame in the area of the compression.

The medial frame extends distally from a base portion, examples of which are described below, to one or more engagement or contacting structures, referred to herein as extensions, at distal end portions of the frame. The extensions are also described more fully below. The frame provides a skeleton or support network for the tip while still allowing flexibility and a measure of a releasable compression at a distal end portion of the catheter, having a flexibility that is different from that of the catheter.

An adaptable tip can have a frame that terminates proximally in a structure that helps to maintain the cylindrical form of the frame during normal use. The terminal structure helps to limit any potential deformation of the tip from being transferred to the catheter once the adaptable tip is positioned on the catheter, such as by welding, bonding or other suitable securement. In one configuration, the terminal structure or base portion 308 is a continuous circular ring at which the helices or struts of a frame are secured or terminate, and in another configuration described below, elements of the adaptable tip extend proximally of the frame and are secured or locked into the marker band 208 or another marker band for a secure engagement between the frame and the marker band. For example, elements of the adaptable tip may include geometries that are compatible with portions of the marker band so that mating elements can snap together or otherwise become engaged for securement. Complementary geometries may include dovetail or key configurations, or other shapes that are compatible or complementary.

The terminal structure can be a base that can take a number of configurations. The base can help to support the tip on a distal end portion of the catheter, and can help to maintain the frame in an approximately cylindrical configuration. In the example illustrated in FIGS. 4-10, the base 308 is a circular ring, extending completely 360° around the circumference of the tip. While the circular ring can be segmented or an assembly of arcuate segments, a solid circular ring helps to securely support the tip as desired. In the present example, the circular ring 308 has the same wall thickness as the helical elements 306 (inside to outside diameter). While the axial length of the circular ring can be the same as that for the helical elements, the axial length of the circular ring 308 is greater than that of the helical elements, so that a transverse cross-section of the circular ring has a greater surface area than a transverse cross-section of one of the helical elements. The circular ring with larger dimensions provides greater support for the tip.

The adaptable tip also includes at least one and in the present examples a plurality of distally-extending engagement or contacting structures, or extensions 310, where the extensions help to engage objects in the vasculature. The extensions extend distally from the medial frame, and have one or more structural features different from the structural features of the medial frame. While they can be different from each other, each of the extensions have identical structural features, and in the illustrated examples they have geometries different from the geometry of the medial frame, and in particular have geometries that are different from sub-elements of the medial frame, such as cells or other sub-elements that constitute a repeating pattern, such as a spiral column in the frame 302. In the present example, the extensions 310 are formed from the same material and by the same cutting procedure (described more fully below) with the same thicknesses as the helical elements 306, but have different geometries. The different geometries provide the different structural features, and in the illustrated example, each extension has a petal or lobe or wing configuration extending axially and distally of the frame and coupled to respective elements of the frame in a way that permits flexing, pivoting or deforming of the petal or lobe or wing about an area near the frame. The material of the extensions allows the extensions to resiliently flex or deform, for example when contacting an object in the vasculature. In the present examples, each extension is independently resiliently flexible relative to the other extensions, and the remainder of the tip helps to otherwise maintain the geometry of the tip while one or more of the extensions are flexed. The mode of flexing is described more fully below.

In the illustrated example, each of the extensions 310 are identical, and only one will be described in further detail. The extension 310 (FIGS. 10 and 11) includes a torsion section 311. The torsion section in the illustrated example is a plurality of components different in geometry from the medial frame and from the wing (described below) allowing the wing to deform differently from the medial frame. The torsion section 311 is supported on the medial frame at nodes 316. The torsion section can take a number of configurations and shapes for flexibility or for torsion, and in the present example includes first and second support elements or torsion bar elements 312 and 314 for supporting the extension on the medial frame 302 and allowing deformation of the extension. They are coupled proximally at respective nodes 316 that interface with the rest of the tip frame. They allow torsional bending of the extension when the extension bends radially outward. They also allow axial movement relative to the uncompressed or neutral configuration of the adaptable tip. The first and second torsion bar elements are coupled to the medial frame at distal ends of respective helical frame elements 306, the junctions of which form the nodes 316. In the present example, the first and second support elements are mirror images of each other, though they need not be, and only one will be described in further detail. The torsion section 311 also includes a bridge element 318 supporting the first support element 312 on a respective node, extending arcuately between the node 316 and the remainder of the first support element 312. The bridge element 318 transitions the first support element to the medial frame 302.

The first support element 312 includes at least one and in the illustrated embodiment a plurality of strut elements, for example first and second strut elements 320 and 322, respectively. In the examples herein, the first and second strut elements extend circumferentially, for example following the wall of an imaginary cylinder that is defined by the tip 300. The first and second strut elements extend in respective planes perpendicular to the axis 304 of the tip, and as illustrated all of the first strut elements for the plurality of extensions are coplanar, and all of the second strut elements for the plurality of extensions are also coplanar. The first and second strut elements have a sufficient length and cross-section allowing the struts to twist or torque when a load is placed on the distal portion of the extension, for example by an embolus or other object in the vasculature, including under aspiration. The torsion section 311 includes a further bridge element 324 connecting the first and second strut elements. As used herein, any described strut elements, including but without limitation the first and second strut elements, characterized or described as straight strut elements are considered "straight" when viewed in side elevation, or if the tip is cut into a planar sheet and placed flat, the strut will be seen as straight. However, when the structure is formed as a three-dimensional geometry, such struts may follow a curvature, for example a curvature of a cylinder in the three-dimensional space that began in some methods of manufacture as a three-dimensional tubular element and becomes a three-dimensional skeletal structure. In both instances, the starting form and the resulting struts will have a curvature.

A distal-most portion of the extension 310 includes a wing 326, which may be described as a skeletal wing having hollow portions, that extends distally in the axial direction and circumferentially between the first and second support elements 312 and 314 of the torsion section 311. The wing 326 offers compliance to the extensions bending radially outward in addition to radial expansability of the entire tip frame in the case that the diameter of the tip frame is expanding (i.e. distance between nodes 316 is increasing). The wing 326 contacts the vascular object and the flexibility of the structures in the extension, including the torsion section 311 with the first and second strut elements 320 and 322 and the corresponding bridge portions 318 and 324, allows the wing to pivot outwardly or move radially outwardly and axially in response to any force or loading arising from the contact with the vascular object. The wing includes a wing frame structure that is relatively lightweight and still able to reliably interact with a vascular object. The wing frame structure includes support segments 328 and a substantially centered element 330, which can contact a vascular object and help to hold or retain the vascular object. In the illustrated example, the support segments 328 extend arcuately from the second strut elements 322 of the torsion section 311 to the centered element 330.

In the present example, the elements of the extensions 310 have substantially the same cross-sectional area and the same wall thickness, for example so that they can all resiliently twist similarly for a given load for contact, for example when contacting a vascular object. When the tip contacts an object, any one or more of the extensions 310 can pivot outwardly, and the wing can pivot by having either or both of the first and second strut elements 320 and 322, as well as the bridge elements 318 and 324, in the torsion section 311 twist in response to any external loading. The support segments 328 can also twist.

In addition to pivoting of the extensions when contacting a vascular object, the medial frame can also resiliently flex upon flexing of the helical elements 306. The medial frame can also compress or can move off-axis, depending on the magnitude and direction of any external loading.

The tip 300, and therefore the medial frame 302, the circular base 308 and the plurality of extensions 310, are monolithic as illustrated, and may be formed from a monolithic tubular element such as a hypo tube or other structure of a desired material and characteristics, such as by laser cutting. The tubular material may be a super elastic nickel titanium alloy that produces a resiliently flexible structure such as those illustrated and described herein. The hypotube or other starting material is configured so that the hypotube has the outer diameter of the tip in its neutral state, namely the desired outer diameter of the tip, in one example the same or approximately the same as the outer diameter of the distal portion of the catheter supporting the tip. Thereafter, the tip is created by the laser-cutting process, and due to the prior treatment of the tube starting material, there will be very little if any potential energy in the final tip configuration, and the tip outer diameter will be approximately the same in its neutral state as the starting material, for example having the dimensions discussed herein or approximately the same as the outer diameter of the distal portion of the catheter supporting the tip. The resulting tip can be resiliently flexible, compact, and easily conform to the structure and geometry of a catheter, including an aspiration catheter. When formed from a tubular material having a uniform wall thickness, the width (in the radial direction) of each of the component elements in the tip will be substantially the same based on the common wall thickness of the starting material. The structural characteristic of any element in the medial frame, the base ring or the extensions will then be based in part on the remaining dimension defining the cross-section of the element. In the example of the tip 300, the cross-sectional area of the circular ring 308 is greater than the cross-sectional area of each of the other elements in the medial frame and the extensions, and the cross-sectional area of each of the elements in the medial frame 302 and in the extensions is substantially the same, except for variations that might occur at transitions such as nodes. In one example of a tip configuration, the cutting of the selected tubular material according to the desired geometry and thicknesses creates axial flexibility and bendability wherein axial compression of between about 20% and 40%, for example, can be visible when under typical vacuum in aspiration applications.

The tip 300, as well as any of the tip configurations described herein, can be used with a catheter for interacting with objects in the vasculature, including changing and/or removing the object, and including without limitation aspiration in conjunction with an aspiration catheter. One or more of the extensions can contact an object, such as an embolus, and possibly move the object. With aspiration, the adaptable tip may help to move or dislodge the object.

In any of the adaptable tips described herein, the tip can be used in conjunction with a catheter where the tip is deployed without any coating, film or barrier between the inside of the tip and the outside of the tip. Alternatively, for example when used as part of an aspiration catheter assembly, the tip can have a coating, film or other barrier, for example made out of a fluid impermeable elastomeric material, for example to help maintain a desired pressure or vacuum within the catheter lumen all the way to the distal-most portion of the tip. All or select portions of the tip can be coated, or otherwise covered with a film or barrier in the inside and/or outside the structure of the tip. In the example of the portion of the assembly shown in FIG. 5, the portion of the tip 300 from the circular ring 308 to points distally beyond the elements of the extensions 310 are embedded in a thin layer of elastomeric polymer 400 to preserve suction or aspiration between the distal-most portion of the tip to the catheter shaft 204. The elastomeric coating can be applied by solvent deposition, and may be a highly elastomeric material, including for example a thermoplastic elastomer, including for example polyurethane, or other highly elastomeric materials, and in one configuration, the material has a SHORE A durometer of approximately 80. The thickness of the layer can be selected as desired, and in one example the thickness may be approximately 0.0012 inch on any surface or between structures, such as between the medial frame elements and between the struts. On the structural elements, such as the helical elements or on the struts, the layer thickness can be approximately 0.0012 inch on each side of the structure, both inside and outside. The resulting assembly of the adaptable tip and the elastomeric film produces an outside surface on the adaptable tip that is not radially uniform, and provides a film that undulates around the structures and provides dips or depressions between structures. A coating, film or other barrier or layer may also take other forms, as desired. In the present example of the tip 300 illustrated in FIGS. 4-10, the film layer extends from the circular base 308 to a circular rim distally beyond the distal-most portion of the extensions 310.

The extensions 310 on the adaptable tip 300 are configured to deform, in some examples at least partly pivoting, in the present examples independently of each other, and in some configurations at least partly independent of the medial frame. One or more of the extensions deform for example when coming into contact with an object in the vasculature to enhance the contact being made between the tip and the object. Deforming the extensions allows additional contact surfaces or greater surface area of contact between the tip and the object. Additionally, in examples where the tip is coated or embedded in a film or layer, deforming the extensions increases the surface area of contact between the object and tip surfaces having the coating, and increases the effective diameter of the assembly to be greater than 0.072 inch, for example even when the lumen ID is 0.072 inch. Deforming the extensions also helps to more easily conform surfaces on the tip to irregular surfaces on the object.

Figure 4:
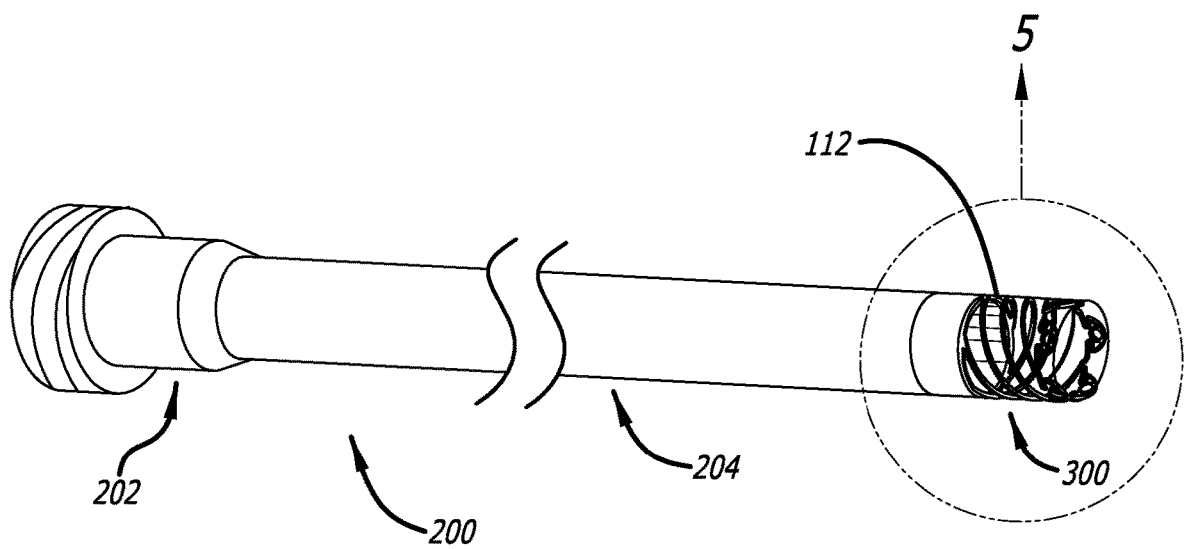
FIG. 4 is a schematic of an aspiration catheter having an adaptable tip.
Figure 6:
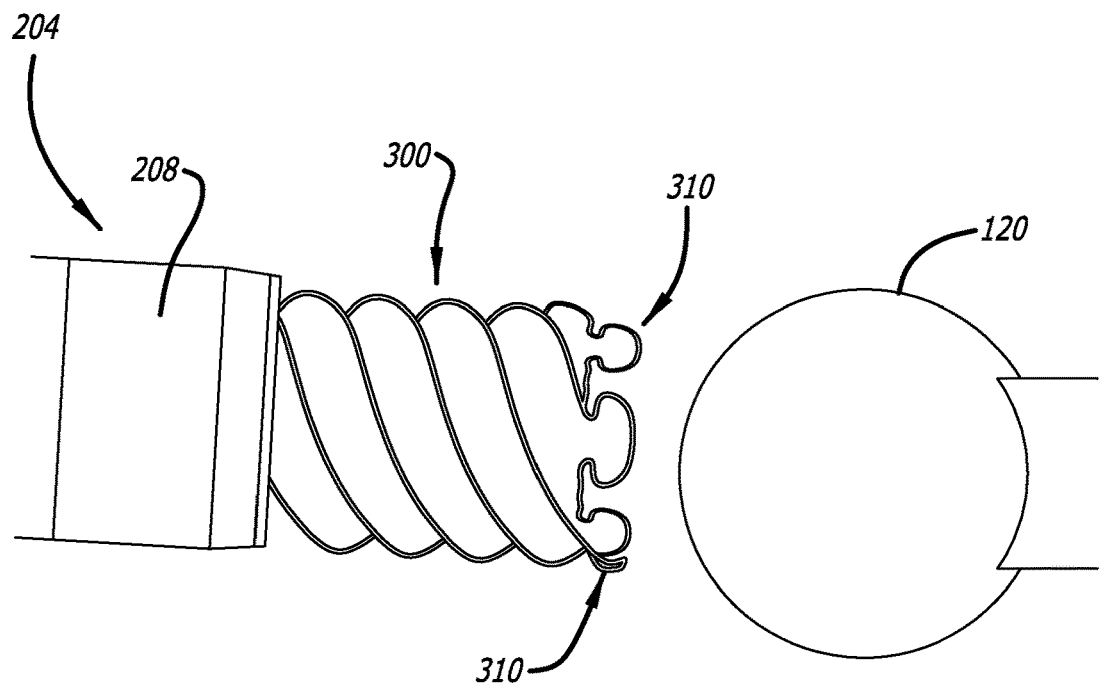
FIG. 6 is side elevation and schematic of the distal portion of the aspiration catheter of FIG. 4 adjacent an object in a body.
Figure 7:
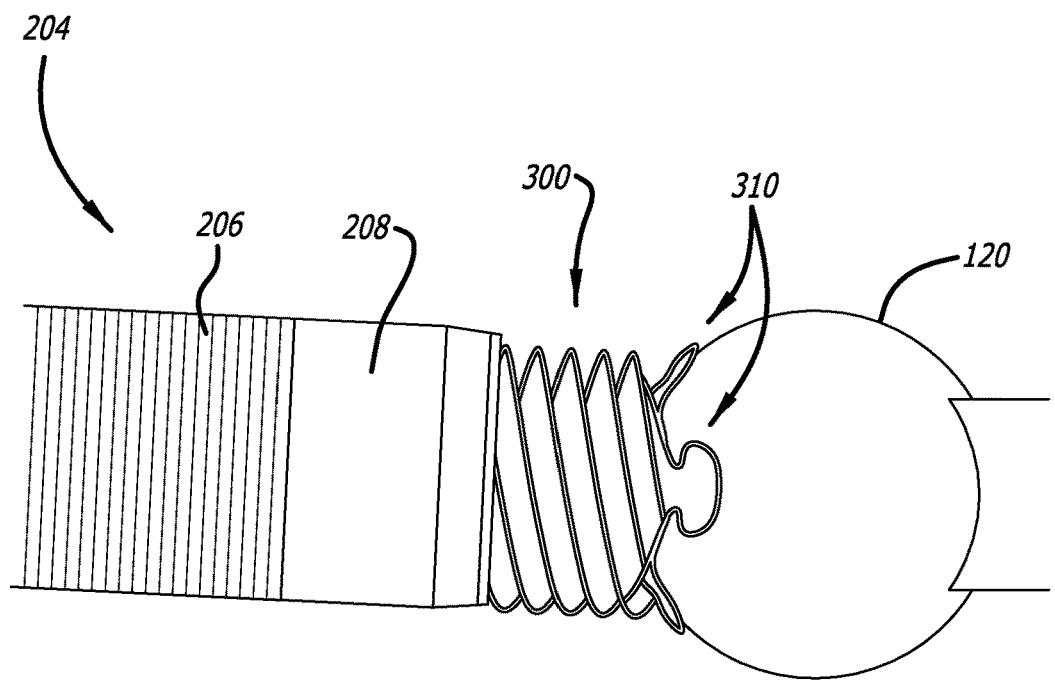
FIG. 7 is side elevation and schematic of the distal portion of the catheter of FIG. 4 in contact with the object shown in FIG. 5 with vacuum applied to the aspiration catheter.
Figure 10:
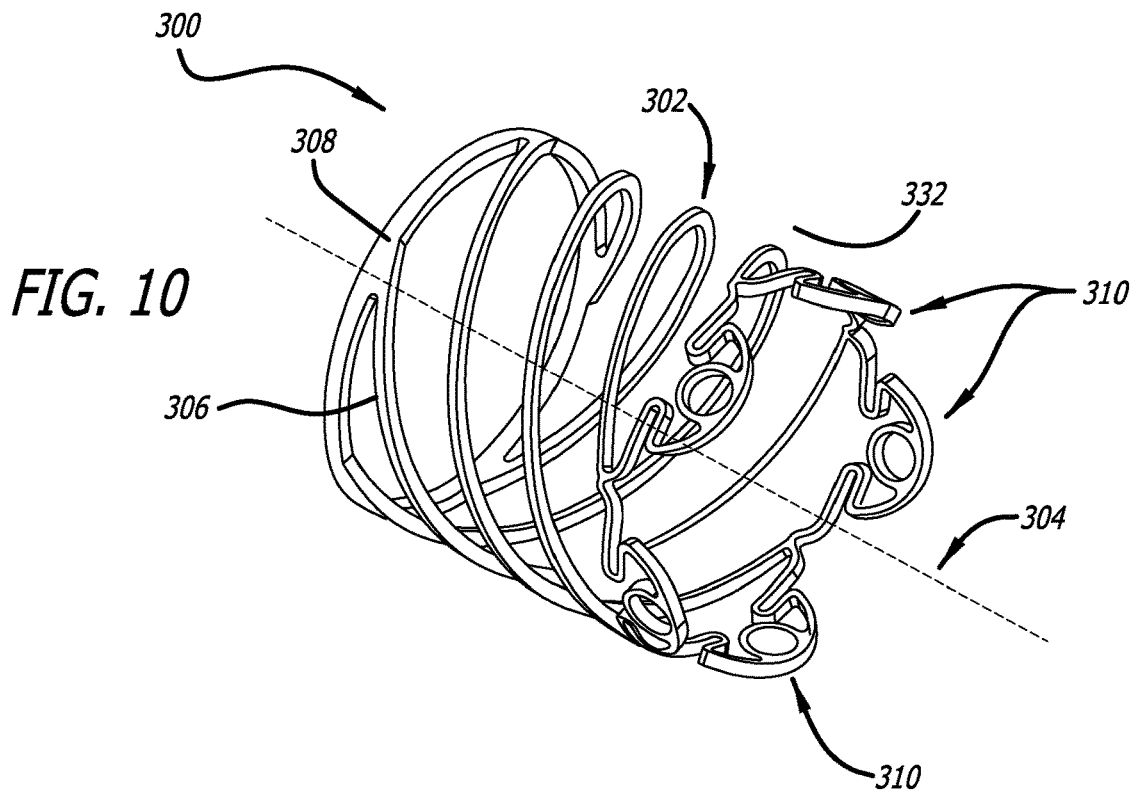
FIG. 10 is an upper right isometric view of an example of an adaptable tip frame and engagement or contacting elements or extensions.
Figure 11:
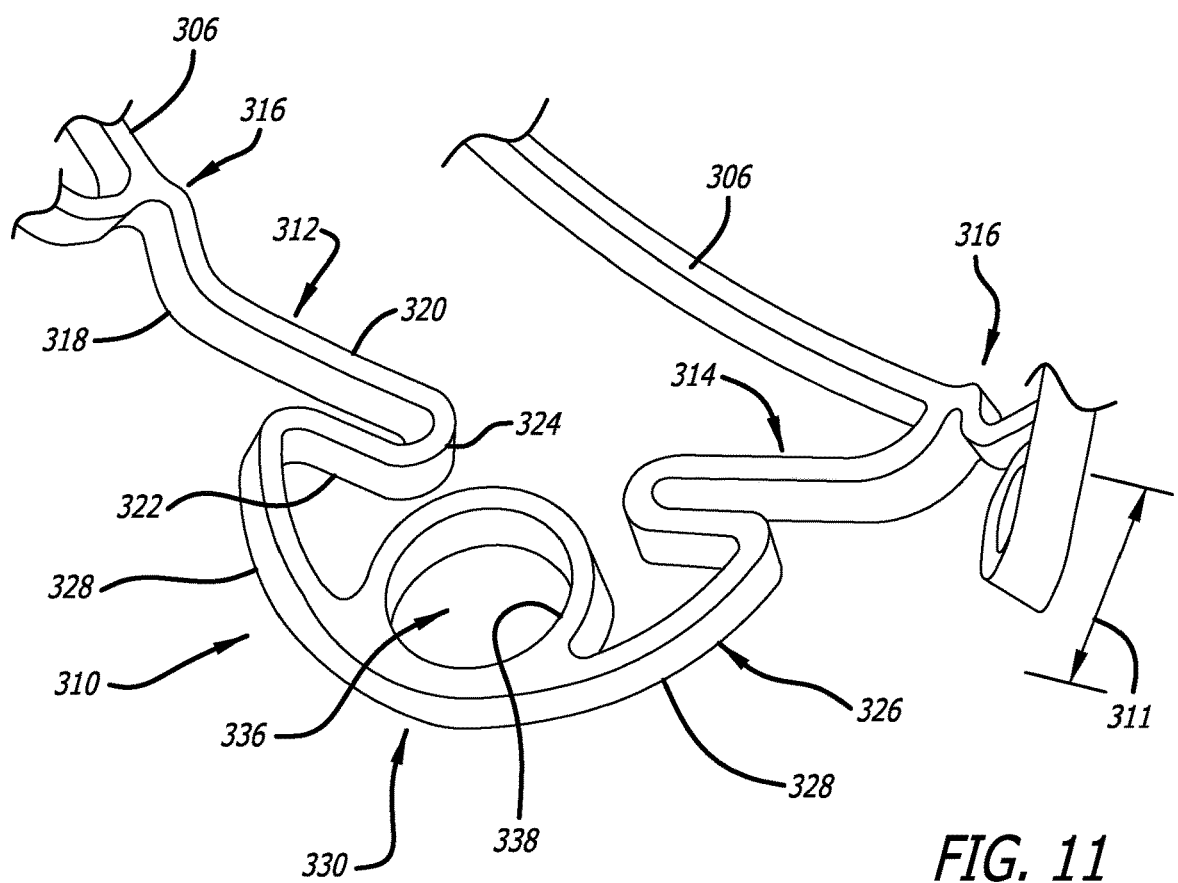
FIG. 11 is a detail view of an extension of the adaptable tip of FIG. 10.

When the catheter with adaptable tip is not engaged with an embolus that is to be removed, it has an un-adapted or neutral configuration as shown in FIGS. 4 and 10. "Neutral" state or configuration refers to the tip in its free and unbiased state or configuration, un-tensioned, uncompressed and unbiased in any direction by any external forces. When the tip is supported by and secured on the catheter, the tip is in a neutral state, being unaffected by any external forces. While it is understood that there may be potential energy in the tip structure, for example arising from its cylindrical shape, which potential energy could be released by cutting the frame longitudinally to let it flatten out, the tip and its assembly on the catheter would be considered in a neutral state when unpackaged and ready for use without any external loads or forces applied, for example as illustrated, for example, in FIGS. 5, 10 and 12. FIG. 6 illustrates the tip in an un-adapted configuration approaching a spherical target 120, which serves as a schematic of an embolus or other object. FIGS. 6 and 7 show the tip without any coating, while it is understood that the tip can include a coating as described herein. FIG. 7 shows the adaptable tip after it makes contact with the spherical target (or embolus), for example during aspiration if the tip is coated, and assumes an adapted or deformed configuration. As illustrated in FIG. 7, the medial frame is compressed and the extensions are deformed. The adapted configuration includes a change in the shape of the tip and the appearance of the extensions so that the extensions deform or bend radially outward to accommodate the embolus being engaged, for example outward about a torsion area, approximately about an axis are such as illustrated at 332 (FIG. 10). This serves to increase and in some cases maximize the surface area of the embolus that is engaged with the tip of the catheter. As the force that a catheter tip can exert on an embolus is directly proportional to the surface area that it is engaged with, having these extensions deform, expand or move outward can serve to improve the mechanical force that a catheter can exert on a given embolus. While not evident in FIG. 7 because the embolus model is presented as having a spherical shape, each extension in their present configurations can act independently to conform to the surface of irregularly shaped embolus, even in examples of complex 3-dimensional shapes. In examples where the extensions are embedded in a film, for example for any of the adaptable tips described herein, the surface area of contact is greater.

Just proximal to the extensions, and as seen in FIGS. 6 and 7, the tip medial frame 302 is designed to have compliance in the axial direction. Compliance or flexibility serves to act similarly to the suspension system on the wheel of a car, where maintaining contact between the wheel and the road is important to maintain control of the car. In this case, maintaining contact with the embolus as the catheter is manipulated can be important because if contact is broken between the catheter tip and embolus, the ability of the catheter to act on the embolus is greatly reduced. The maintenance of contact is helpful in the axial direction as well as in the case of off-axis contact or bending between the catheter and embolus. The helical elements 306 in the frame 302 serve to act as the "suspension" as described above with axial movement along the axis 304, and also serves to provide support and ensure that the lumen within the tip frame remains open when vacuum for aspiration is applied, when used with an aspiration catheter. Without this support in an aspiration application, the walls of the adaptable tip could collapse radially inward, occluding or affecting aspiration, and affecting or preventing removal of the embolus. Additional to axial flexibility, the tip frame also may be bendable to be therefore better suited to accommodate off-axis bending while maintaining contact between the extensions and the embolus. In one example, the axial flexibility and bendability may be achieved when the tip is configured to have axial compression of between about 20% and 40%, for example, that can be visible when under typical vacuum in aspiration applications.

The extensions 310 may but need not also include radiopaque markers fixedly attached to provide fluoroscopic guidance as to the shape and configuration of the extensions during use. In some configurations, such markers may give information about the shape and configuration of the adaptable tip and/or of the adjacent object as well. The adaptability of the tip, for example in an aspiration catheter design, with movable markers provides visual feedback to the user during use. Conversely, with non-adaptable catheter designs, the radiopaque marker band 208 does not change visually if engaged or not engaged with an embolus. The user is unable to determine if the catheter is engaged with an embolus based on fluoroscopic imagery alone.

Any of the adaptable tips described herein can be used with or without a fluid impermeable film, coating or barrier, and without markers additional to the fixed marker 208. Alternatively or additionally, any of the adaptable tips described herein can include one or more markers on respective movable elements of the tip. In one example of a marker on a movable element of the tip, a tip 300A (FIGS. 8-9) is identical to the tip 300 except for the inclusion of a marker 334 on at least one and preferably each of the extensions 310A. Each marker is secured in a respective opening 336 (FIG. 11) such as defined by a cage 338 in the substantially centered portion 330. In the illustrated configuration, the markers 334 are flat circular discs secured in the respective openings, but in an alternative, they may be concave and conforming to the curvature of the assembly in the shape of a cylinder. With markers, any movement of any one or more of the extensions can then be visible through fluoroscopic imaging, allowing the physician to evaluate the positional changes in the extensions 310, relative to the neutral state, and/or relative to the fixed marker 208, which gives situational information beyond catheter tip location. Situational information includes information more than catheter positional information, and includes any one or more of the existence and location of objects such as emboli, characteristics of such emboli such as contour and size, how the tip has adapted to the object, whether the object can be maneuvered with the tip and whether the object might become disengaged from the adaptable tip, and if so at what stage of the engagement. In an example of possible disengagement, for example under aspiration, disengagement might be observable if the compressed tip becomes less compressed. This might be observed even if the object is still engaged with the tip, for example if the object is engaging an adjacent surface that is at least in part counteracting the suction from the catheter, which would moderate the tip compression arising from the vacuum to the extent of the counter force arising from the other engagement of the object. The marker gives information relative to the extension and its neutral state, and relative to the standard marker 208. Moreover, the torsion section with the struts and its physical characteristics for deformation allows the user with experience to appreciate or evaluate the characteristics of the object that causes any deformation. Because of the structural characteristics of the extensions, deflection of an extension under normal circumstances will not occur randomly or with incidental movement of the adaptable tip through the vasculature, but upon contact or engagement with a significant object such as embolus, and to a greater extent when accompanied by the force of aspiration. Therefore, markers on deformable extensions on a catheter tip provide a strain gauge function for the user, both for magnitude and direction.

Additionally, the relative rigidity of the adaptable tip having markers on deformable extensions gives confidence to the user that the tip will remain in the neutral configuration under normal operating conditions unless the tip is affirmatively acted upon by an external object, such as an object in the vasculature, for example embolus. This confidence applies whether the adaptable tip is inside a guide catheter or outside, because the tip geometry will be the same in both conditions unless the tip is being acted upon by an object, for example by deforming an extension or by bending or compressing a medial frame. For example, deformation, bending or compression during aspiration in vasculature will be a function of the size, position and other characteristics of the embolus, and not a function of whether the tip is inside or outside a guide catheter. The circular base ring 308 and the sizes of the components in the medial frame 302 and the extensions 310 help to maintain the cylindrical shape of the adaptable tip during normal operation until a vascular object such as an embolus places a load on a part of the tip. Simply moving from inside a guide catheter to outside a guide catheter, or from outside a guide catheter to inside a guide catheter, would not change the geometry of the adaptable tip because the adaptable tip is in a neutral state in both configurations absent a vascular object applying a load to part of the adaptable tip.

Figure 8:
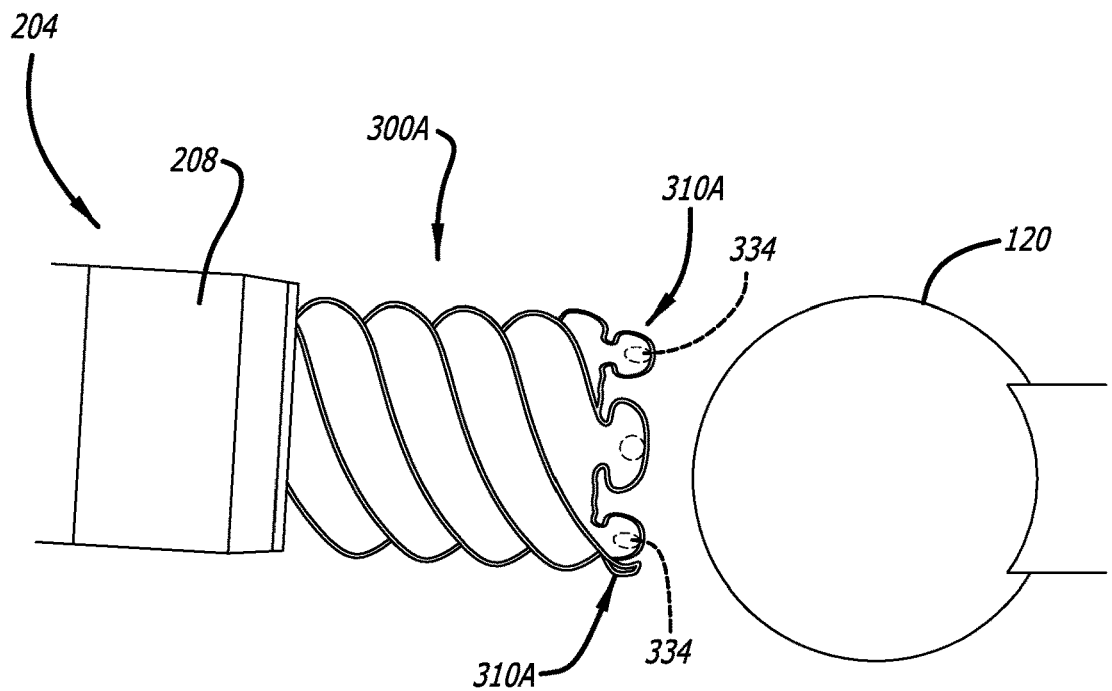
FIG. 8 is side elevation and schematic of a distal portion of an aspiration catheter adjacent an object in the body and having visualization markers on a distal portion of an adaptable tip.
Figure 9:
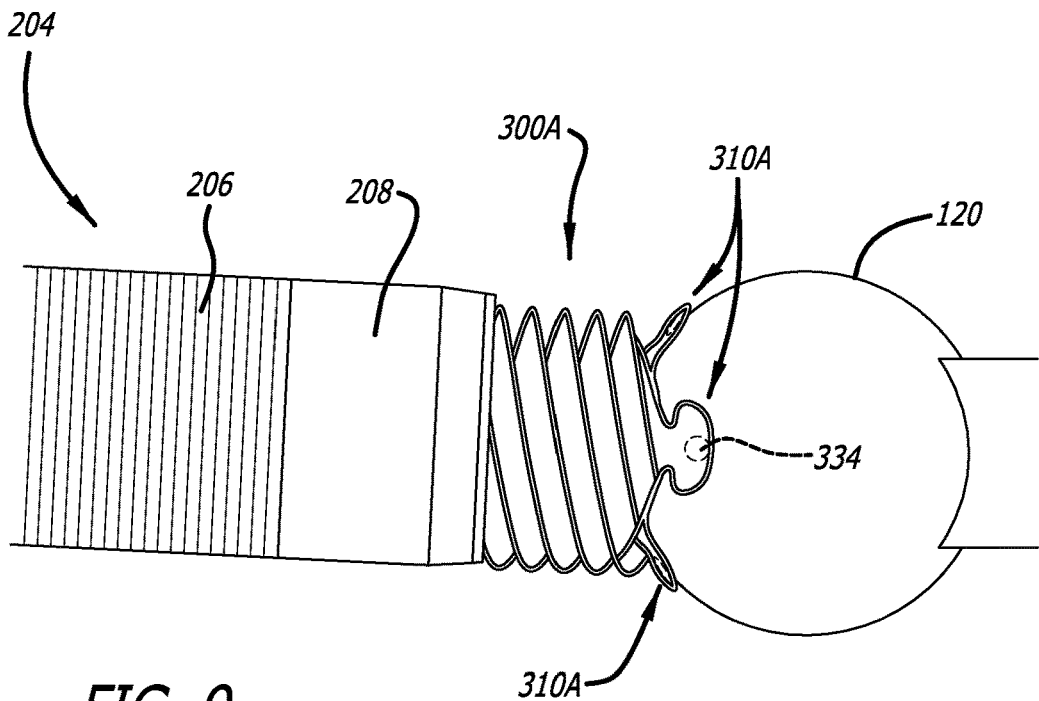
FIG. 9 is side elevation and schematic of the object of FIG. 8 with the adaptable tip in contact with the object and visualization markers arranged over the object based on rearrangement of engagement or contacting elements or extensions on the adjustable tip supporting the markers.

As illustrated in FIGS. 8 and 9, the relative positions of the various markers on the catheter shaft and on the extensions can be visualized. The movements, reactions or deformations of the extensions discussed with respect to FIGS. 6-7 also apply to a tip with markers 334, with the added benefit of visibility as illustrated in FIGS. 8-9. The markers reveal the difference in mechanical configuration of the distal tip between being non-adapted or neutral and being adapted, respectively. Where the tip includes five extensions on the medial frame, the markers 334 in a neutral state show as points on a circle a first distance distally from the fixed marker 208. With deformation as illustrated in FIG. 9, the circle defined by the markers 334 fall on a circle of a slightly larger diameter and the circle defined by the markers is axially closer to the fixed marker 208. The schematic object 120 is spherical, but with an asymmetric object, one or another or multiple extensions 310A are deformed radially outward, though not all extensions or not to the same extent, and the extensions may also be axially closer to the fixed marker 208, which changes may be visualized for evaluating the form of the object as well as its position relative to the catheter. The illustrations of FIGS. 8 and 9 depict on-axis configurations, while similar comments apply to off-axis engagements between an object and the adaptable tip. These differences in mechanical configuration could be visualized by the user and decisions about when to retract the catheter or otherwise manipulate the catheter could be made based on this visual feedback, which is a further advantage of the adaptable tip catheter over a non-adapting one, and of a tip having movable markers over a tip having no additional markers.

It has been noted that the tip medial frame 302 having helical elements oriented on the same direction help to act as a "suspension" with axial movement along the axis 304, and also helps to provide support and help the lumen within the tip frame remain open when vacuum for aspiration is applied. In an alternative, a modified medial frame can be used in any of the adaptable tip configurations described herein. In one example, an alternative tip 300B has a medial frame 302A (FIG. 12) that can have helical elements extending in both a first direction as in the tip 300, and in a second direction. In the illustrated example, the medial frame 302A has helical elements 306A extending in the first direction and also has helical elements 340 in the second direction crossing the first helical elements 306A. Their pitches are the same magnitude but they are considered opposite. The first helical elements of the medial frame 302A are labeled "306A" because they are not structurally identical to the helical elements 306 in the medial frame 302 in that they are not geometrically continuous from the base 308 to the distal end portions at the extensions 310. Instead, the continuity of the original helical elements 306 is interrupted at intersections with the opposite helical elements 340, but they otherwise have similar structures and functions as the helical elements 306. The alternative medial frame may be considered to have a plurality of helical elements 306 and 340 formed of a plurality of struts 342, adjacent ones of which are connected at nodes, for example nodes 344. In the illustrated example, the nodes are a combination of the strut ends that join at the node and a bridge portion 346 extending between strut ends. While first and second helical elements can be formed into a medial frame without the bridge portions 346, so that crossing helical elements form a simple "X" pattern, the bridge portions help in the structural integrity of the medial frame. With the bridge portions, which in the illustrated configuration extend in respective planes perpendicular to the central axis 304 but can extend in respective planes parallel to the central axis, the bridge portions join adjacent longitudinally extending wave elements. In the configuration illustrated in FIG. 12, there are 10 wave elements, each one extending longitudinally from the circular base 308 to respective ones of the extensions 310. Alternatively, if the bridge portions extend in respective planes parallel to the central axis 304, they would connect wave elements extending circumferentially about the axis 304, and there would be five wave elements stacked axially.

Figure 12:
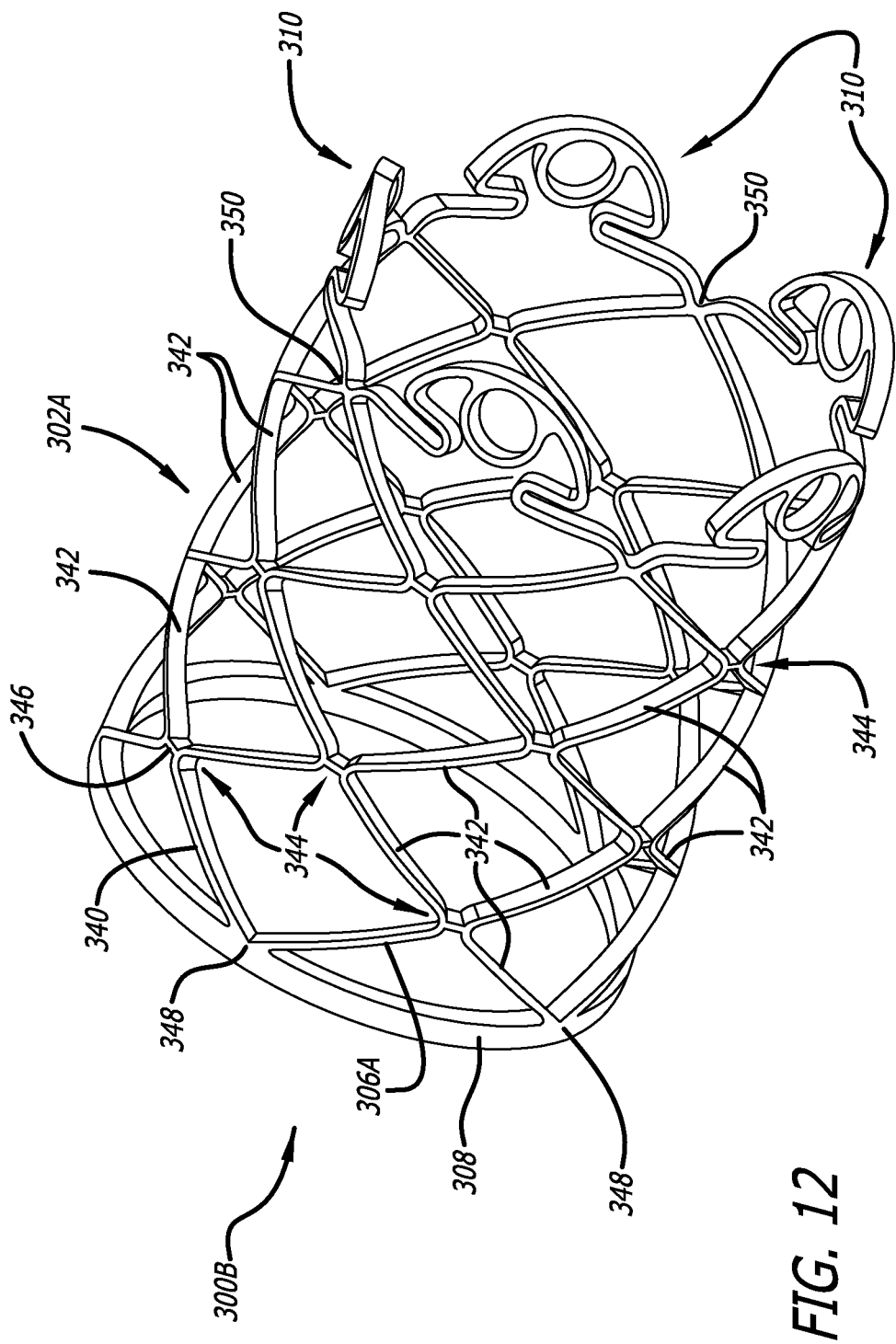
FIG. 12 is an upper right isometric view of another example of an adaptable tip frame and engagement or contacting elements or extensions.

The struts create a plurality of cells or windows each of which approximate a parallelogram shape, or half of a parallelogram at the boundaries. As used herein, "parallelogram" or "parallelograms" in the context of the struts of the frame means a geometry or geometries formed by struts if the struts were co-planar and in a neutral state, for example if the frame were converted to a sheet and extended flat, whereas in the structure created for the tip frame, the structure is created from a monolithic tube, for example laser cut from hypotube, which starts and finishes with the shape of a cylinder. The finished tip frame struts appear to form parallelograms when viewed in plan view in a neutral state, but the tip frame is 3-dimensional rather than flat. The windows are formed by the plurality of struts in which respective struts are connected at the nodes 344. A benefit of the pattern shown in FIG. 12 is that during axial compression, for example when contacting an object and/or during aspiration, the diameter of the adaptable tip will increase similarly to how a tubular braid increases in diameter as it is axially compressed. The increase in diameter further helps to engage emboli and increases the probability that it will be aspirated and removed, including when extensions or petals or lobes are included on the frame.

In the illustrated configuration, the adaptable tip 300B has the same circular base ring 308 and the same extensions 310. Pairs of opposite helical elements join the base 308 at nodes 348. The extensions 310 are supported on the same first helical elements 306A at nodes 350 (FIG. 13), and second helical elements 340 intersect respective ones of the same nodes 350. In another example of an adaptable tip such as that illustrated in FIG. 12 as 300B, the adaptable tip 300B can include one or more markers in the extensions (not shown) in the same manner as was discussed with respect to the adaptable tip 300A. The structure and function of the extensions, with or without markers, is substantially the same as that described with respect to the extensions 310/310A herein. In further alternatives, another support structure can be substituted for the circular base ring 308 and/or other configurations of extensions, with or without markers, can be substituted for the extensions 310/310A. Additionally, in the configuration of the adaptable tip 300B illustrated in FIG. 12, the combination of the circular base, the struts intersecting at nodes and the extensions being supported at respective adjacent nodes renders the medial frame as a closed cell mesh or network, which helps to enhance the structural integrity of the medial frame. As with any of the adaptable tips described herein, the adaptable tip 300B with or without markers can be coated with or embedded in a fluid-impermeable elastomeric film, for example to help maintain a pressure differential across the tip.

In one example of the medial frame 302A, the struts 342 and the bridge elements 346 are configured to have substantially the same cross-sectional area. Additionally, the struts 342 in the medial frame and the struts 320 and 322 in the extensions (FIG. 11) are also configured to have substantially the same cross-sectional area. Also, the wing 326 is formed from elements having cross-sectional areas substantially the same as the struts 320 and 322, and if the wing includes a marker holding frame or structure, elements of the marker holding frame, for example the arcuate strut elements 328, can have cross-sectional areas substantially the same as the struts 320 and 322.

The medial frame can also be configured so that different portions of the frame tend to have different axial deformations. In such a configuration, axial compression of the frame could result in a frame configuration that is bent, all other things being equal, or having a tendency to be bent according to the frame configuration. Such a configuration may help to more reliably hold an object that is oriented off of the central axis of the frame. Additionally, different axial deformations might be selected to produce a desired visible compression, for example compression of between approximately 20% and approximately 40%, or compressions outside such a range as may be desired.

The extensions for any of the adaptable tips described herein can take a number of configurations. As noted previously, the extensions can include a leaf, pedal, lobe or wing configuration having a wing skeleton or frame that can deform through torsion elements when a load is applied, for example from an object in the vasculature, including for example during aspiration. Additionally, the extensions may include markers as described herein for visualization, and they may be embedded in an elastomeric fluid impermeable film or layer.

In any of the adaptable tip configurations described herein, the tip may have one or more extensions, for example an odd number of extensions, for example 5 as illustrated, that may interact with an object in the vasculature. The extension may have a body that is larger (boundary-wise, or has a larger aspect), more rectilinear, or extend over a greater arc length, or otherwise have a different geometry than the extensions 310 described herein.

In one example of an alternative extension configuration for an adaptable tip 300C (FIGS. 14-16), the medial frame 302A has a network of repeating cells with a first geometry, described herein as approximating parallelograms, and extensions 310B have a second geometry different from the first geometry. In the present example, the second geometry is rectilinear. As illustrated, the tip includes an odd number of extensions, namely five extensions, all of which are identical and only one of which will be described in detail, but one or more may be different from the others. The extension includes an arcuately extending wing 352 coupled to and supported by the nodes 350 of the medial frame (FIG. 16) through a torsion section 311, including torsion bars 312 and 314 and bridges, which have the same structure and function as previously described with respect to the extensions 310 other than linear dimensions to accommodate the different geometry of the arcuately extending wing 352. The torsion elements 312 and 314 extend circumferentially and extend in respective planes perpendicular to the axis of the tip, and are coupled to the wing 352 by respective bridge elements 354.

Figure 13:
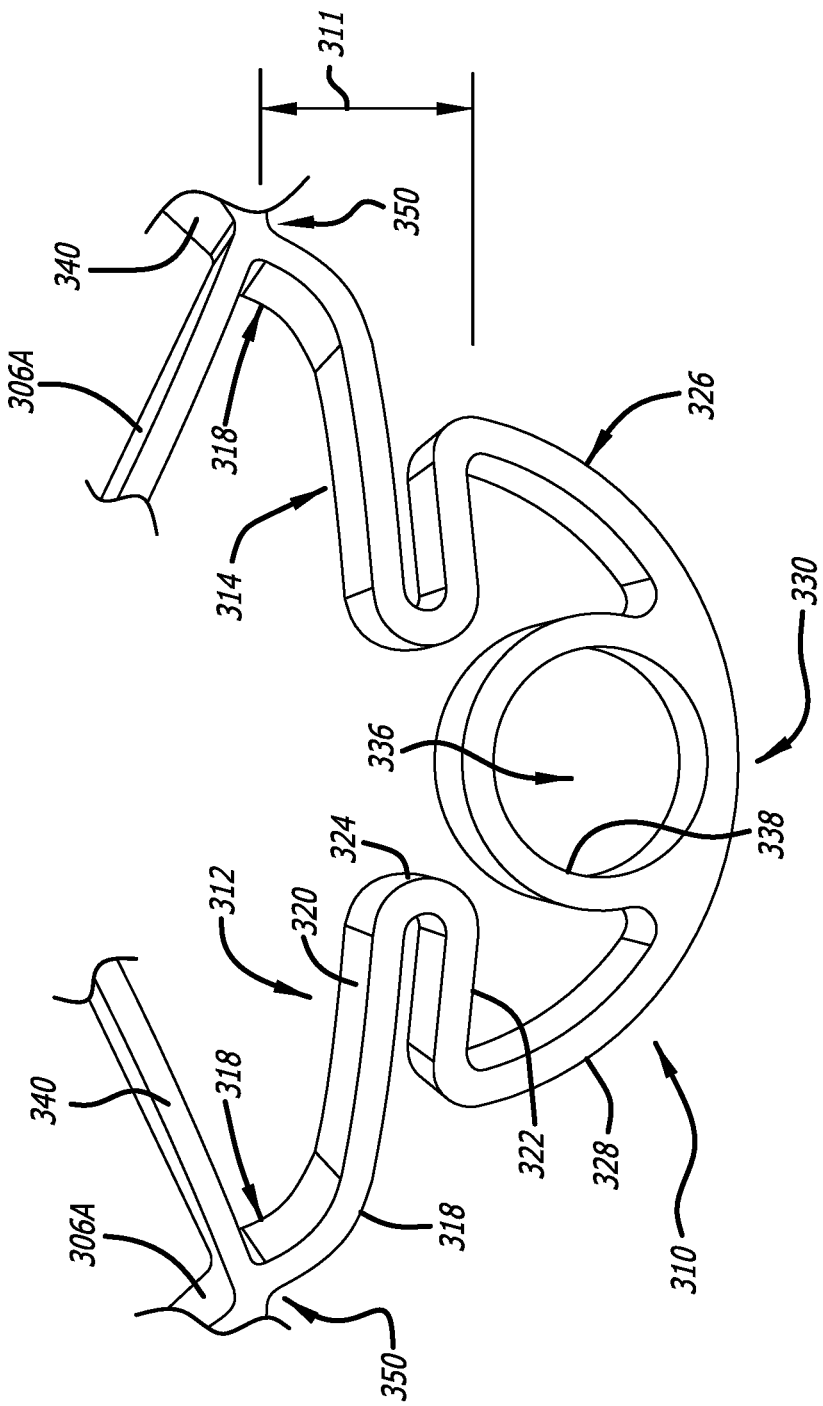
FIG. 13 is an upper detail view of an extension used on the example in FIG. 12.

In the present example, the arcuately extending wing 352 extends a first distance 356 along a line in a plane perpendicular to the tip axis greater than a second distance 358 along a line in a direction parallel to the tip axis. This geometry gives a wider arc of potential contact with a vascular object without significantly increasing the overall axial length of the tip relative to the distal end portion of the catheter. Additionally, the relatively shorter distance 358 helps to minimize any trauma to the surrounding body lumen arising from the deformation of the extensions in the radial direction. In one configuration, the first distance is greater than twice the second distance, and in one example is approximately four times the second distance. The wing 352 has a distal segment 360 (FIG. 16) that is the distal-most portion of the wing and has a longer extent in the arcuate direction than the wing 326 (FIG. 13). This longer extent increases the probability of the wing 352 contacting an object in the vasculature compared to the wing 326.

Figure 15:
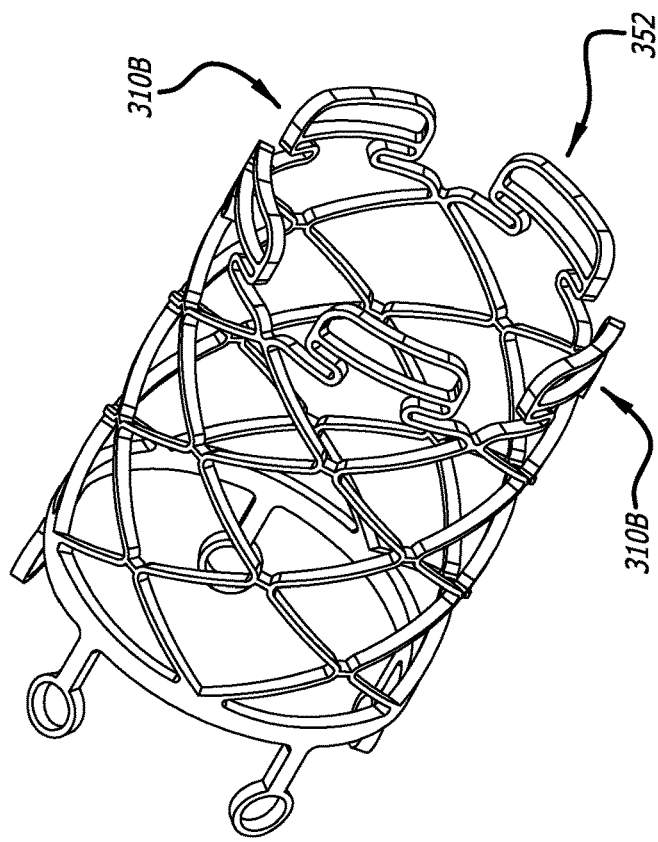
FIG. 15 is an upper front isometric view of the tip of FIG. 14.
Figure 14:
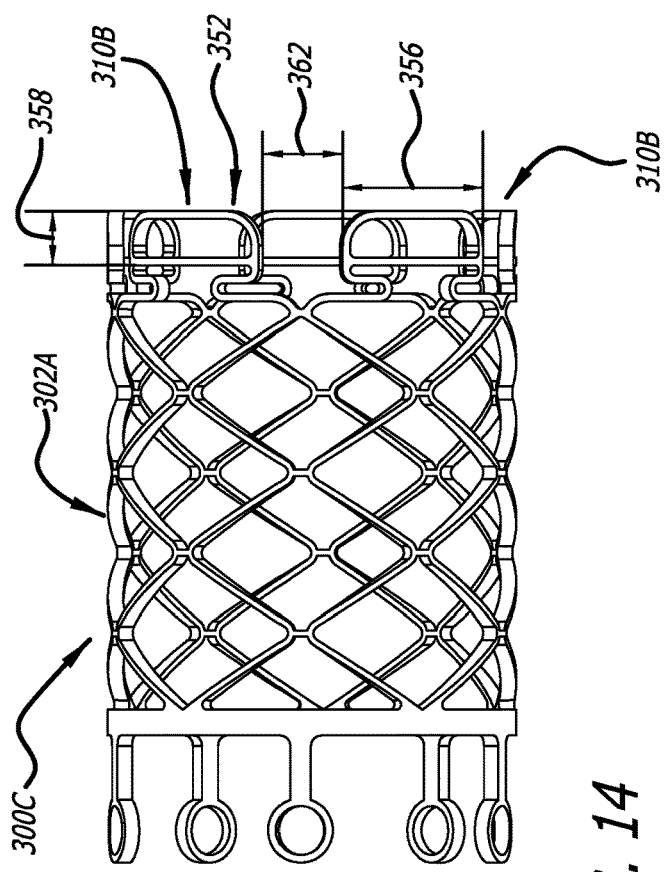
FIG. 14 is a side elevation view of another example of an adaptable tip having securement features, a tip frame and engagement or contacting elements or extensions.
Figure 16:
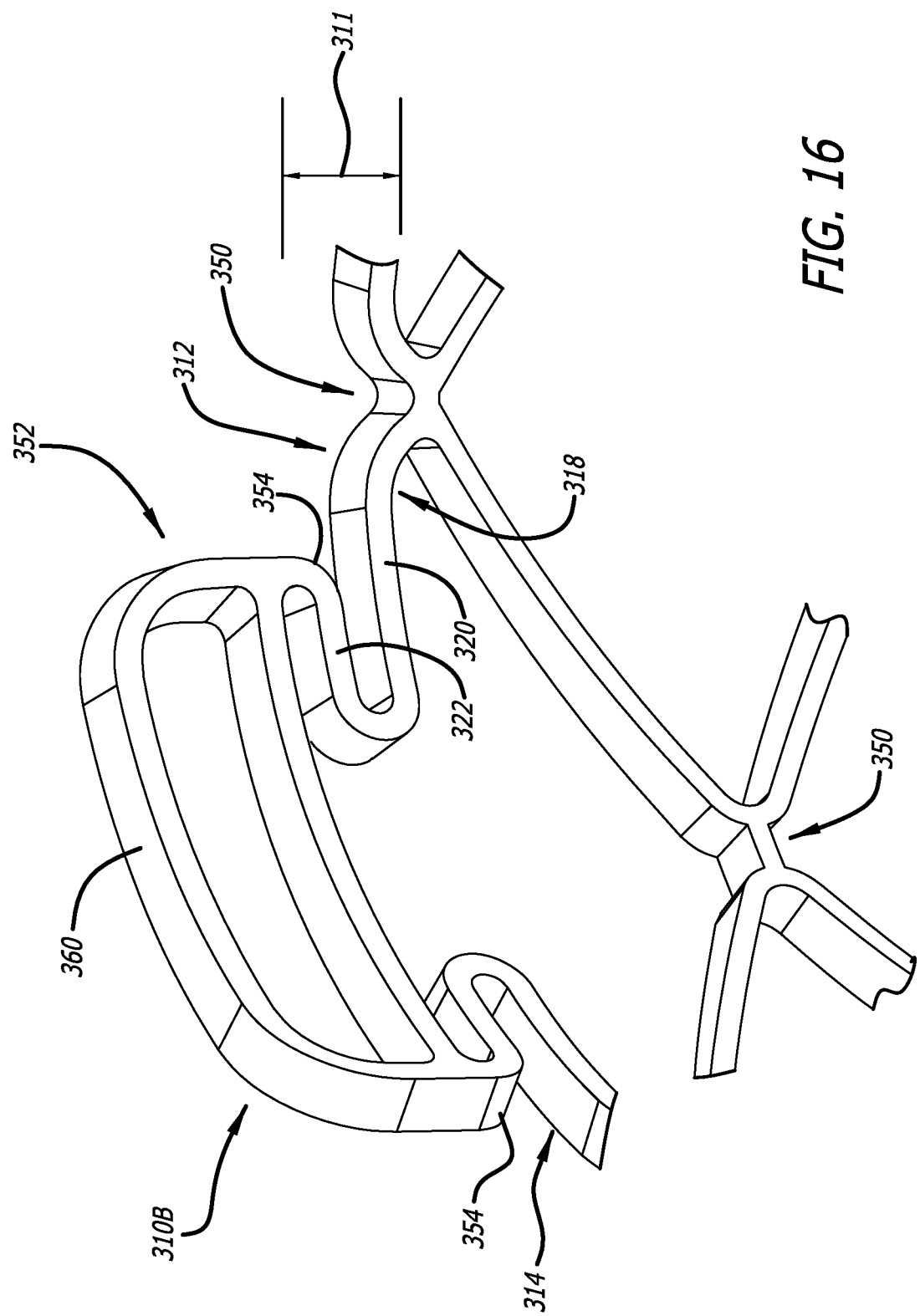
FIG. 16 is a detail view of an extension of the adaptable tip of FIG. 14.

As with any of the adaptable tips described herein, the adaptable tip 300C can have at least a portion covered or coated with or embedded in an elastomeric film, and if desired a fluid impermeable polymeric film (not shown in FIGS. 14-16). If such a film is included, it will be configured substantially the same as other films discussed herein for coating the adaptable tip. For a given film configuration, the flexibility or deformability of the extensions 310B may depend on the arcuate length 356 of the wing 352 relative to the gap 362 (FIG. 14). The wider the gap, the easier it is for the wing 352 to deform. In one configuration, the ratio of the width of the wing 352 to the width of the gap is greater than or equal to approximately one and less than or equal to approximately six. A ratio of 2 has been found to be desirable.

In the illustrated configuration of the extensions 310B, the wings 352 are flexible radially outwardly and somewhat axially, given the configuration of the torsion section 311 and the associated torsion elements. The wings 352 are also somewhat movable arcuately or circumferentially, also given the characteristics of the torsion elements and because there are no structures preventing such movement. However, deformation of the wings radially outward is a preferred form of deformation, and a range of motion in radial deformation is greater than a range of motion of the wing circumferentially. In other words, the extensions 310B have a greater flexibility radially outwardly than circumferentially. The wings 352 also have a larger aspect than the wings 326, and provide a larger element for contacting and engaging a vascular object.

In an additional or alternative configuration, any of the adaptable tips described herein can include a non-circular radiopaque marker. A plurality of non-circular markers provides more information to the user under fluoroscopy, for example when there is deformation of even one extension with a marker. For example, a plurality of non-circular markers is seen as a more pronounced or more visible element than a circular marker, for example even where one dimension of the non-circular marker is the same as a diameter of the circular marker. Additionally, if one dimension of the non-circular marker extends in a circumferential direction, a plurality of such markers will appear as more of a circular marker band, for example a continuous marker band, the deformation of which is more easily visible, even if deformation is of a single extension. Additionally, circular marker bands are more familiar geometries under fluoroscopy, so a combination of arcuately extending markers more closely approximating a circle will appear more normal than 5 circular dots separated by large gaps approximating a circle, for example. Upon deformation, movement of one or more non-circular markers may produce the appearance of flaring in an originally circular pattern, which will give information about the shape or other characteristics of the object causing the deformation. For example, the original circular pattern may change to a bulge or flared curvature in one portion of the marker combination, and one or more markers may separate into discrete images separate from the remainder of the original circular pattern. Additionally, deformation may produce the appearance of an angularity in the flare, in an orthogonal view, which helps the user to visualize characteristics of the object causing the deformation. Furthermore, deformation producing the appearance of an angularity in the flare combined with a change in the spacing between the original circular pattern of the plurality of markers and the marker ring 208 may indicate how securely the object is engaged with the extensions. The orientation of any flare or change in the appearance of the original circular pattern, such as by differing deformation by different extensions, can also indicate whether the object is engaging the tip on axis or off axis, and possibly how stable the engagement is. Therefore, a plurality of non-circular markers may more easily provide desired information than circular markers.

The extensions on adaptable tips can have respective non-circular markers where at least one is different from the others or all are different from each other, which may contribute to a more helpful resolution of information arising from deformation of portions of the adaptable tip. In an illustrated configuration, all of the non-circular markers on the extensions have the same geometry. For example, an adaptable tip 300D (FIGS. 17-18) has extensions 310C having geometries identical to the extensions 310B but wherein the wings 352 contain non-circular markers 364. The structures and functions of the extensions 310C are substantially the same as those for the extensions 310B except to the extent that the solid markers 364 add structural support/rigidity to the wings 352. The extensions 310C and respective markers 364 also can be used on any of the other adaptable tip configurations described herein.

Alternatively or additionally, the marker 364 is nonplanar. The marker in one configuration conforms to a curvature of the adaptable tip, which defines a cylinder of a radius about the central axis 304, and the marker includes a concave surface 366 and a convex surface 368 wherein the convex surface faces outward and the concave surface 366 faces inward toward other markers in the assembly. An arcuate marker may provide an aspect for the viewer that provides more information than a flat marker, circular or noncircular, for example when differentiating between the visible image in a neutral configuration and the visible image in a deformed or non-neutral configuration. A bottom 370 of the marker has a substantially flat surface while a top 372 includes a flat surface extending to rounded corners 374, giving the marker an approximately rectilinear side profile but for the rounded corners 374. The rounded corners make the marker asymmetric about a plane through the marker transverse to the central axis 304.

The non-circular marker 364 can have a major axis 376 and a minor axis 378, wherein the minor axis is shorter than the major axis, and in the present example the major axis extends circumferentially while the minor axis extends parallel to the tip axis 304. Therefore, the minor axis is substantially straight whereas the major axis 376 follows the curvature of the cylindrical shape of the tip. In the illustrated example, the major axis is greater than twice the minor axis, and can be four or more times the minor axis. This and other geometries of non-circular markers can be described using other geometric nomenclature, and it is understood that the noncircular marker 364 is not exactly rectilinear, both because it is nonplanar and because it has rounded corners. However, the relatively long major axis combined with those of the other non-circular markers of the same geometry on the other extensions combine to produce an almost completely circular visual band upon fluoroscopy, and in an orthogonal view it may appear completely circular without any gaps, for example as may be visualized in FIG. 17. With deformation or flaring of one or more extensions, the transition from a normally circular geometry to a flare or bulging geometry is readily visible, allowing the user to better evaluate the characteristics of any object engaging the adaptable tip. Therefore, non-circular markers give more information to the user than circular markers, rectilinear markers give more information to the user than circular markers, and extensions having different marker geometries can provide more information than extensions having only circular or only identical non-circular markers.

Any of the adaptable tips described herein can include any of the base configurations, medial frames, or extensions described herein, with or without markers and with or without a fluid impermeable film. An example of such a base configuration may include a base ring 380 (FIG. 17) substantially the same and engaging and supporting the medial frame 302A substantially the same as described with respect to the base rings 308, including combining with helical elements or struts at nodes as described herein. The structure and function of the base ring 380 is substantially the same as the base rings 308 described herein.

In the present example illustrated in FIGS. 14 and 17, the base ring further includes at least one and in the present example a plurality of proximally-extending supports or extensions 382. In the illustrated example, the base ring includes an odd number of supports, in the present example 5 supports, only one of which will be described in detail. In other configurations, one or more of the supports can be different from others of the supports. The supports engage an adjacent portion of the catheter, and help to secure the adaptable tip to a distal end portion of the catheter. The support includes a linear portion 384 extending proximally from a proximally-facing surface of the ring 380, and a nonlinear portion 386 at a proximal end of the linear portion. In the present example, the nonlinear portion 386 is a hollow circular element 388 positioned on the linear portion 384 on a diameter of the circular element. The linear and nonlinear portions of the support help to engage complementary surfaces in respective portions of the adjacent catheter. In other examples, the supports can have other geometries for reliably securing the adaptable tip on the adjacent distal portion of the catheter.

Figure 19:
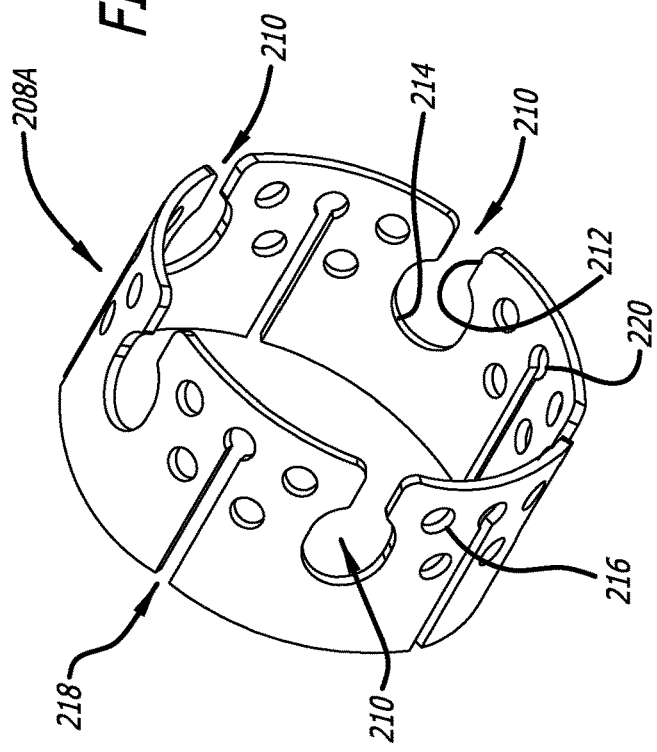
FIG. 19 is an isometric view of a securement ring for a catheter for helping secure and adaptable tip on the catheter.
Figure 20:
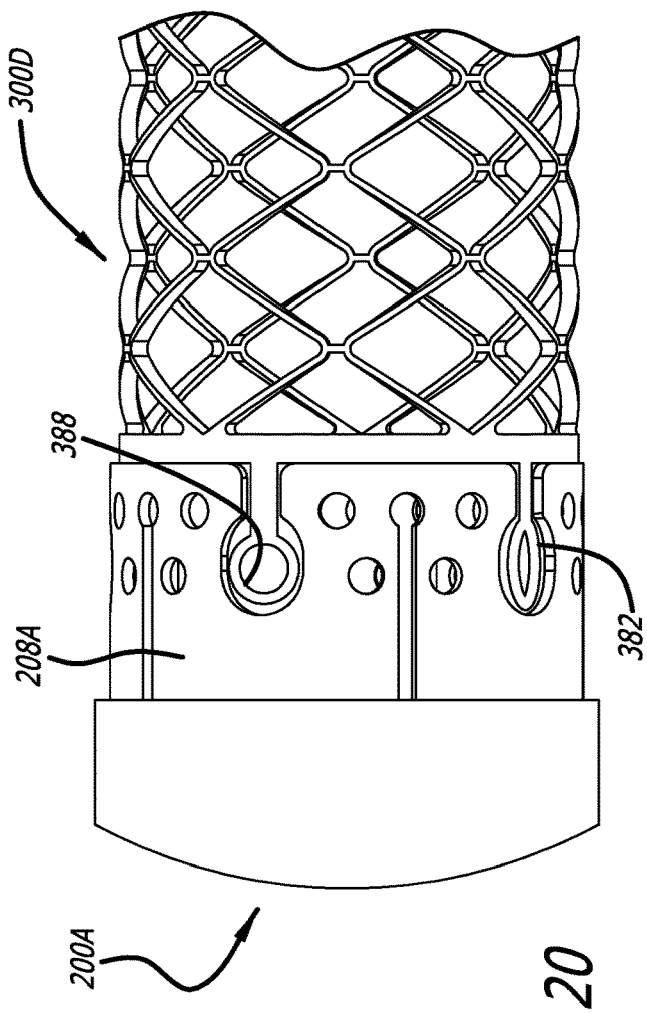
FIG. 20 is a side elevation and detail view of the securement ring of FIG. 19 on a distal portion of a catheter supporting an adaptable tip.

The base ring 380 and its extensions 382 can be supported and secured on an adjacent distal portion of a catheter 200A (FIG. 19-21) to provide an adaptable tip 300D on a catheter, for example an aspiration catheter. The tip 300D can be mounted on such a catheter by conventional methods.

In another configuration, the base ring 380 and its extensions 382 can be supported and secured on an adjacent distal portion of a catheter 200A using a profiled ring 208A (FIGS. 19-20), which in the present example is formed from a radiopaque material. The profiled ring 208A serves as a supporting element for the adaptable tip 300D and as a marker ring in the manner of conventional marker rings such as marker 208. The profiled ring includes a plurality of key openings 210 formed in a distal rim, having profiles at least partly complementary to the extensions 382. In the illustrated configuration, the key openings include longitudinal slots 212 approximately complementary to the linear portions 384 and partially circular portions 214, approximately complementary to the nonlinear portions 386. The key openings help to support and secure the adaptable tip 300D to the catheter, and to help assembly of the adaptable tip on to the catheter through alignment of the extensions 382 with the key openings 210. The extensions 380 to interengage with the key openings. The adaptable tip 300D may also be secured in place in the profiled ring through welding, a biocompatible adhesive, or by a plastic film or coating wherein the plastic embeds itself in the openings of the nonlinear portions 386 and between the adjacent surfaces of the extensions 382 and the key openings 210.

The profiled ring 208A may also include a plurality of openings 216 formed through wall portions of the profiled ring. It may also include a plurality of slots 218 formed in a proximal rim of the ring, terminating in substantially circular openings 220.

A catheter assembly 200A (FIG. 21) can be formed in a conventional manner with a hub 202 and a catheter body 204 formed over a mandrel 222. The profiled ring 208A is mounted on a distal portion of the catheter body, and the adaptable tip 300D is engaged to the profiled ring by expanding the nonlinear portions 386 and passing them over the outside of the profiled ring until they enter or snap in place in the corresponding openings 210, either before or after the profiled ring is placed on the distal portion of the catheter body. The profiled ring and the adaptable tip are then secured together, for example by welding, adhesive or a suitable polymer. The catheter assembly can then be used as is after removal of the mandrel, or all or portions of the adaptable tip 300D are embedded in a suitable elastomeric film or coating, for example a fluid impermeable coating, such as by vapor deposition. The catheter assembly can then be used after removal of the mandrel, including as an aspiration catheter, for example to remove vascular objects, including emboli. Alternatively, a catheter assembly can be assembled with any of the other adaptable tips described herein, with or without markers and with or without an elastomeric film, in a manner similar to that described with respect to FIG. 21, for example either with a profiled ring 208A or with a conventional marker ring and secured in place through adhesive or other suitable means.

The catheter assembly 200A, with any of the adaptable tips described herein, can be assembled or fitted with a protective cover 500 on a distal portion of the catheter and covering the adaptable tip. The cover 500 helps to protect the distal end portion of the catheter and the adaptable tip during packaging, shipping and preparation for use. The cover may be a suitable plastic, for example polyethylenetetraphthalate.

A catheter assembly having any of the adaptable tips described herein with or without an elastomeric film can be used to evaluate vascular objects such as emboli, and if suitable remove the object, for example by either aspiration or by withdrawing the object with the adaptable tip. In one example, a distal portion of the catheter with the adaptable tip is advanced in a vessel, for example using fluoroscopy to monitor the location of the distal portion of the catheter using a conventional or modified ring marker. The catheter can be advanced inside a guide catheter to a desired location, and then the tip in a neutral configuration advanced outside the guide catheter, and the tip would remain in the neutral state after leaving the guide catheter until reaching a vascular object. In another example, the catheter can be advanced as an assembly combined with a navigation catheter extending through the internal lumen of the catheter 204 and distal of the adaptable tip. In the area of a vascular object, the adaptable tip can be advanced beyond the distal end of the navigation catheter (and/or concurrent with removal of the navigation catheter from inside the catheter 204) and maneuvered against the object, deforming one or more extensions on the adaptable tip. If used in conjunction with aspiration, a reduced pressure can be applied to the lumen of the catheter, for example using the aspiration system 104, and the object aspirated through the lumen or is biased against the adaptable tip, with extensions on the adaptable tip contacting the adjacent surfaces of the object. The object may then be removed with retraction of the catheter assembly.

In another example of such a method, a catheter assembly having any of the adaptable tips described herein with markers, with or without an elastomeric film, can be used to evaluate vascular unwanted objects such as emboli, and if suitable remove the object. The object may be aspirated through the lumen of the catheter or the object may be removed by withdrawing the object with the adaptable tip. The distal portion of the catheter with the adaptable tip is advanced in a vessel, for example using fluoroscopy to monitor the location of the distal portion of the catheter using a conventional or modified marker. The catheter can be advanced inside a guide catheter to a desired location, and then the tip in a neutral configuration advanced outside the guide catheter, and the tip would remain in the neutral state after leaving the guide catheter until reaching a vascular object. In another example, as described above, the catheter can be advanced as an assembly combined with a navigation catheter extending through the internal lumen of the catheter 204 and distal of the adaptable tip. In this example as well, the tip maintains its neutral configuration while over the navigation catheter and after, until it contacts an object. The markers on the extensions of the adaptable tip can be monitored for any deformation outside the guide catheter, possibly indicating a vascular object. With any deformation, either of the extensions and/or of the medial frame, the characteristics of the object can be evaluated, and if suitable the object removed either by aspiration or by removal of the adaptable tip. During the procedure, the user can evaluate any deformation of the markers on the extensions, for example as described herein, to help evaluate the characteristics of the object and determine a desired course of action. In some cases, stopping of forward motion does not necessarily mean that an embolus has been encountered, so the present apparatus with markers on deformable extensions can be used to evaluate why forward progress has been affected. In some cases, the object can be aspirated through the lumen, and in other cases the object can be withdrawn through the vessel with the adaptable tip.

Having thus described several exemplary implementations, it will be apparent that various alterations and modifications can be made without departing from the concepts discussed herein. Such alterations and modifications, though not expressly described above, are nonetheless intended and implied to be within the spirit and scope of the inventions. Accordingly, the foregoing description is intended to be illustrative only.

What is claimed:

1. A movable hollow tip for a distal end of an aspiration catheter, the tip comprising
    a support ring having a solid annular element and a plurality of proximally-extending projections wherein at least one of the plurality of proximally extending projections includes a hollow circular end portion,
    a plurality of struts wherein adjacent struts are coupled to each other at respective nodes and wherein a plurality of nodes are coupled to the support ring and wherein the plurality of struts form a plurality of parallelograms extending circumferentially to form the shape of a cylinder,
    a plurality of extensions wherein each of the plurality of extensions is coupled to respective first and second nodes of adjacent nodes at distal portions of respective parallelograms, wherein each of the plurality of extensions includes at least first and second extension struts extending in a plane perpendicular to an axis of the tip when the tip is in a neutral state and
    at least one nonplanar radiopaque marker distal of the first and second extension struts, and
    a fluid impermeable coating over the plurality of extensions and the plurality of struts forming a cylindrical wall and extending distally beyond distal end portions of the plurality of extensions.

2. The tip of claim 1 wherein the support ring and the cylinder of the plurality of parallelograms have substantially the same outer diameters when the tip is in the neutral state and unconstrained circumferentially.

3. The tip of claim 1 wherein the at least one marker is non-circular.

4. The tip of claim 1 wherein the at least one marker is one of a plurality of markers and wherein each marker extends arcuately a first distance and axially a second distance and wherein the first distance is greater than the second distance.

5. The tip of claim 4 wherein the first distance is greater than twice the second distance.

6. The tip of claim 1 wherein the at least one marker is asymmetric about a plane bisecting the at least one marker and the plane is perpendicular to the tip axis.

7. The tip of claim 1 wherein the at least one marker extends a first distance in a plane perpendicular to the tip axis greater than a second distance in a direction parallel to the tip axis, and wherein the first distance is substantially four times the second distance.

8. The tip of claim 1 wherein the at least one marker includes a width extending circumferentially and wherein adjacent markers are separated by a gap and wherein a ratio of the marker width to the gap is greater than or equal to substantially one and less than or equal to substantially 6.

9. The tip of claim 1 wherein each extension extends arcuately a third distance and adjacent extensions of the plurality of extensions are spaced apart by a gap extending a fourth distance, and wherein a ratio of the third distance to the fourth distance is greater than or equal to one and less than or equal to six.

10. The tip of claim 1 wherein the at least first and second struts in each of the plurality of extensions includes at least one strut extending in a circumferential direction.

11. The tip of claim 1 wherein at least one extension of the plurality of extensions has a first range of motion circumferentially and a second range of motion radially, and wherein the second range is greater than the first range of motion.

12. The tip of claim 1 wherein at least one extension of the plurality of extensions has a first flexibility circumferentially and a second flexibility radially, and wherein the first flexibility is less than the second flexibility.

13. The tip of claim 1 wherein each of the plurality of extensions is pivotable about a respective axis that is substantially on a chord of a cylinder defined by the tip in the neutral state and includes at least one of the extension struts extending arcuately and at least partly on the chord.

14. The tip of claim 1 wherein the plurality of struts forming the shape of a cylinder define a plurality of openings extending at least partly circumferentially and the coating extends into the openings.

15. The tip of claim 1 wherein the tip is formed from nitinol and has a hollow cylindrical shape.

16. A catheter assembly comprising an aspiration catheter having a catheter body having a distal end portion and a movable hollow tip according to claim 1 supported on the distal end portion of the aspiration catheter.

17. The catheter assembly of claim 16 wherein the distal end portion has a first outer diameter and the support ring has a second outer diameter substantially the same as the first outer diameter.

18. The catheter assembly of claim 16 wherein the catheter body defines a lumen having an inside diameter at the distal end portion and wherein an inside diameter of the tip is substantially the same as the inside diameter of the catheter lumen.

19. The catheter assembly of claim 16 further including an annular element supported on the distal end portion, wherein the annular element includes walls forming key openings for receiving portions of respective ones of the projections of the tip.

20. The catheter assembly of claim 19 wherein the annular element is formed of a radiopaque material.

* * * * *